United States Patent [19]

Ross et al.

[11] Patent Number: 4,526,718
[45] Date of Patent: Jul. 2, 1985

[54] 3,3-DI(ACYLTHIO)-2(4-ALLYLTHIOAZETIDIN-2-ON-1-YL)PROPENOIC ACID ESTER COMPOUNDS

[75] Inventors: Barry C. Ross, Luton; Graham Johnson, Milton Keynes, both of England; Michael A. Yeomans, Liederbach, Fed. Rep. of Germany

[73] Assignee: Hoechst UK Limited, Great Britain

[21] Appl. No.: 524,977

[22] Filed: Aug. 22, 1983

Related U.S. Application Data

[63] Continuation of Ser. No. 318,113, Nov. 4, 1981, Pat. No. 4,474,793.

[30] Foreign Application Priority Data

Nov. 6, 1980 [GB] United Kingdom ............... 8035657

[51] Int. Cl.³ ............... C07D 205/08; C07D 513/04; C07D 499/00
[52] U.S. Cl. ............... 260/239 A; 260/245.2 R; 544/5
[58] Field of Search ................... 260/239 A

[56] References Cited

PUBLICATIONS

Ernest, Chem. Abs. 95, 169105k (1981).

Primary Examiner—Mark L. Berch
Attorney, Agent, or Firm—Curtis, Morris & Safford

[57] ABSTRACT

What are disclosed are compounds, useful as intermediates in the preparation of substituted penem compounds, of the formula

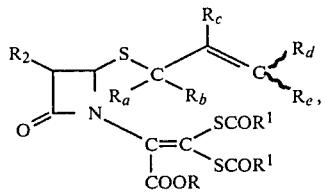

wherein R is a removable esterifying group, $R^1$ is lower alkyl or phenyl, $R^2$ is hydrogen, lower alkyl, lower alkoxyalkyl, lower alkanoyloxyalkyl, or tri-lower alkylsilyloxyalkyl, and $R_a$, $R_b$, $R_c$, $R_d$, and $R_e$ are hydrogen, aliphatic cycloaliphatic hydrocarbon, free or esterified carboxyl, halo, or cyano, and any two of $R_a$–$R_e$, taken together, may form a cycloaliphatic ring.

1 Claim, No Drawings

3,3-DI(ACYLTHIO)-2(4-ALLYLTHIOAZETIDIN-2-ON-1-YL)PROPENOIC ACID ESTER COMPOUNDS

This is a continuation application of application Ser. No. 318,113, filed Nov. 4, 1981 now U.S. Pat. No. 4,474,793.

This invention relates to substituted 7-oxo-4-thia-1-azabicyclo[3,2,0]heptane and 7-oxo-4-thia-1-azabicyclo[3,2,0]hept-2-ene derivatives.

7-oxo-4-thia-1-azabicyclo[3,2,0]heptane has the following structure:

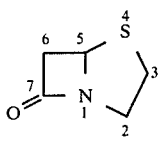

The present invention provides a compound of the general formula Ia and its tautomer Ib

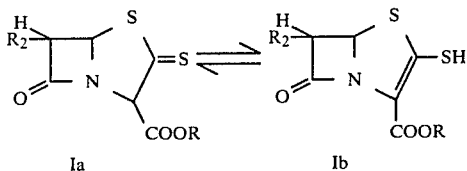

in which formulae
R represents a carboxyl esterifying group, and $R^2$ represents hydrogen or an aliphatic group. More preferably
$R^2$ represents hydrogen, lower alkyl, lower hydroxyalkyl, lower alkoxyalkyl, lower acyloxyalkyl or trilower alkylsiloxyalkyl,
and salts thereof.

The terms "a compound of the general formula I" and "a compound of formula I" are both used hereinafter to denote a compound of the general formula Ia, a compound of the general formula Ib, or any mixture thereof.

$R^2$ may be cis or trans to the carbon-sulfuric moiety at position 5. The stereochemistry at position 5 can be R or S i.e. a compound of formula I may be 5R, 6R, 5R, 6S; 5S, 6R or 5S, 6S. It is preferable, however, to have the 5R stereochemistry, (as defined by the CahnIngold-Prelog system of nomenclature). A chiral carbon atom is also present at position 2 in formula Ia, giving further R and S isomers.

The present invention also provides a process for the production of a compound of the general formula I, which comprises treating a compound of the general formula II

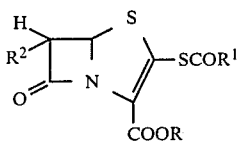

in which R and $R^2$ are as defined above, and $R^1$ represents a lower alkyl group or a phenyl group and represents especially a methyl group, with a nucleophilic compound and, if desired, carrying out any one or more of the following steps in any desired order:

(a) converting a free acid of formula I into an ester thereof, (b) transesterifying a compound of formula I, (c) converting a free acid or an ester of formula I into a salt, or a salt into the free acid, an ester, or another salt, (d) removing any protective groups present other than an esterifying group R.

The treatment of the compound of formula II with a nucleophilic compound is generally carried out in a solvent, and in some cases the solvent itself may also function as the nucleophilic compound.

There can be used either an organic nucleophilic compound or an inorganic nucleophilic compound. Examples of inorganic nucleophilic compounds are water, alkali metal and alkaline earth metal hydroxides, carbonates and bicarbonates, for example, sodium hydroxide, sodium carbonate, sodium bicarbonate, potassium carbonate, potassium bicarbonate, and magnesium carbonate; borates and phosphates.

Organic nucleophilic compounds are, for example, amines, for example, primary and secondary aliphatic amines, for example, ethylamine, methylamine, diethylamine, and dimethylamine; cycloaliphatic amines, for example, cyclohexylamine; non-aromatic heterocyclic amines, for example, morpholine, piperidine and piperazine; aromatic heterocyclic amines, for example, pyridine and substituted pyridines, for example, 4-N,N-dimethylaminopyridine, imidazole and substituted, especially lower alkyl substituted, imidazoles, for example, methylimidazole; aromatic amines, for example, aniline and substituted anilines, for example, methyl-substituted anilines, for example, toluidine; and hydrazine and hydroxylamine. Preferred are heterocyclic nitrogen bases having a pK between 5 and 9, particularly aromatic nitrogen bases. Most preferred is imidazole.

As mentioned above, the treatment of a compound of formula II with a nucleophilic compound is generally carried out in a solvent. In some cases the solvent itself may function also as the nucleophilic compound, as is the case with water.

The solvent is, for example, a water-miscible ether, for example dioxane or tetrahydrofuran; an alcohol, for example, having up to 4 carbon atoms, for example, methanol, ethanol or propanol; water; an amide for example dimethylformamide, dimethylacetamide, or hexamethylphosphoramide; or dimethylsulphoxide, acetonitrile or sulpholane.

A mixture of any two or more solvents may be used, for example, a mixture of water and another solvent, for example, an amide, an alcohol, or an ether.

When the nucleophilic compound is, for example, an alkali metal borate or phosphate salt, this is preferably used in the form of a solution thereof in water or in a mixture of water and another solvent, the solution having a pH within the range of from 8 to 11. If the nucleophilic compound is an amine having a pK greater than 7, it is preferable to buffer the reaction mixture so the pH is within the range of from 6 to 8, for example, using Sorenson's phosphate buffer or Clark and Lubs's borate buffer.

Preferred nucleophilic compounds are alkali metal hydroxides, carbonates and bicarbonates, especially sodium carbonate, and aromatic heterocyclic amines, especially imidazole. A preferred solvent is a water/dioxan mixture, preferably comprising from 1 to 50% by volume of water in dioxan, especially from 5 to 25% water in dioxan.

The reaction is generally carried out at a temperature within the range from the freezing point of the solvent or solvent mixture or −10° C. (whichever is the higher), to 50° C., preferably from 0° to 25° C.

The reaction mixture comprising the resulting compound of formula I is preferably diluted with water or an aqueous acid for example aqueous citric acid, so the resulting mixture has a pH of from 1 to 4, and extracted into an organic solvent, for example, an ester, for example, ethyl acetate or a halogenated hydrocarbon, for example, chloroform. The resulting compound of formula I is then generally pure enough for further use, but if desired, it may be purified further, for example by crystallisation or chromatography.

In the compounds of formulae I and II, $R^2$ preferably represents a hydrogen atom, or an unsubstituted or substituted, straight or branched chain aliphatic group. An aliphatic group may be a straight or branched chain lower alkyl, alkenyl or alkynyl group, for example, a methyl, ethyl or vinyl group.

The term "lower" as used herein in all instances denotes a molecule, group or radical having up to 8 carbon atoms, and especially up to 4 carbon atoms.

Unless stated otherwise, halogen atoms are fluorine, chlorine, bromine and iodine atoms.

A heterocyclic group preferably has up to 4 heteroatoms, which may be the same or different, selected from nitrogen, oxygen and sulphur atoms, and up to 14 atoms in total.

The term "known" means in actual use in the art or described in the literature of the art.

An aliphatic group $R^2$ may be substituted, if desired, by one or more substituents, which may be the same or different. Examples of substituents are halogen atoms; hydroxyl groups; alkoxy and alkylthio groups; alkylcarbonyl groups; carboxy, alkoxycarbonyl and alkylthiocarbonyl groups; alkanoyloxy and alkanoylthio groups; nitro, cyano and azido groups; amido and imido groups; amidino and guanidino groups; imino, amino, mono- and dialkylamino, mono- and diarylamino groups, and N,N-alkylarylamino groups; acylamino groups; carbamoyl and carbamoyloxy groups, and carbamoyl and carbamoyloxy groups substituted on the nitrogen atom by one or two groups selected from alkyl and aryl groups, and the corresponding unsubstituted and substituted groups in which the oxygen atom or each or either oxygen atom is replaced by a sulphur atom.

Any substituent of $R^2$ that is itself capable of substitution may be substituted, for example, by any one or more of the substituents described above.

Preferred substituents for an aliphatic group $R^2$ are hydroxyl groups, which may themselves be substituted for example, by one of the following groups: —$R^3$, —CO—$NR^3R^4$, —CO—$R^3$, —CO—$OR^3$, —$SO_2$—$R^3$, —$SO_2NH_2$, and —$SO_3H$, —$SiR_3R_4R_5$, in which groups $R^3$, $R^4$ and $R^5$, which may be the same or different, if more than one are present, each represents an alkyl group, especially a lower alkyl group, an aryl group or an aralkyl group, especially an aryl-lower alkyl group. Furthermore, the nitrogen atom present in the group —CO—$NR^3R^4$ may be part of an aromatic or non-aromatic heterocyclic ring.

$R^2$ especially represents a hydrogen atom, a lower alkyl group, or a hydroxyl-lower alkyl group, for example, a methyl, ethyl, hydroxymethyl, 1-hydroxyethyl (R or S) or 2-hydroxyprop-2-yl group, or a vinyl group.

An esterified carboxyl group —COOR is, for example, an ester formed with an unsubstituted or substituted aliphatic, cycloaliphatic, cycloaliphatic-aliphatic, aryl, araliphatic, heterocyclic or heterocyclic-aliphatic alcohol having up to 20 carbon atoms, or is, for example, a silyl or stannyl ester.

R may represent, for example a straight or branched chain substituted or unsubstituted alkyl, alkenyl or alkynyl group having up to 18 carbon atoms, preferably up to 8 carbon atoms, and especially up to 4 carbon atoms, for example, a methyl, ethyl, n-propyl, iso-propyl, n-butyl, sec-butyl, iso-butyl, tert-butyl, n-pentyl, n-hexyl, allyl, or vinyl group.

An aliphatic group R, especially a methyl group, may be substituted by a cycloalkyl, aryl or heterocyclic group, or R may itself represent a cycloalkyl, aryl or heterocyclic group.

A cycloaliphatic group R may have up to 18 carbon atoms and is, for example, a cyclopentyl, cyclohexyl or adamantyl group. An aryl group may have up to 12 carbon atoms and may have two or more fused rings. An aryl group R is, for example, an unsubstituted or substituted phenyl group, and an unsubstituted or substituted phenyl group, and an unsubstituted or substituted aralkyl group is, for example, a benzyl, p-nitrobenzyl or benzhydryl group.

A heterocyclic group may have one or more heteroatoms, selected from oxygen, nitrogen and sulphur, and up to 14 atoms in total. A heterocyclic group is, for example, an oxygen-containing heterocyclic group, for example, a tetrahydropyranyl or phthalidyl group.

A stannyl group R may have up to 24 carbon atoms, for example, R may represent a stannyl group having three substituents, which may be the same or different, selected from alkyl, alkenyl, cycloalkyl, aryl, aralkyl, alkoxy and aralkoxy groups, for example, alkyl groups having up to 4 carbon atoms, for example, n-butyl groups, phenyl and benzyl groups, especially three n-butyl groups.

A silyl group R may also have up to 24 carbon atoms and three substituents, which may be the same or different, selected from alkyl, alkenyl, cycloalkyl, aryl and aralkyl groups, for example, alkyl groups having up to 4 carbon atoms, for example, methyl and t-butyl groups.

Any group R that is capable of substitution may be substituted. Examples of substituents are given above in relation to $R^2$. Substituents for phenyl groups are, for example, as described above in relation to $R^2$.

The group R may be removable by hydrolysis, by photolysis, by reduction or by enzyme action to give the free acid, or two or more methods may be used, for example, reduction followed by hydrolysis. A group R that may be removed readily without substantial degradation of the rest of the molecule is particularly useful as a carboxyl protecting group. Examples of esters that are readily split by reduction are arylmethyl esters, for example, benzyl, p-nitrobenzyl, benzhydryl and trityl esters. Reduction of an ester, for example, an arylmethyl ester, may be carried out using hydrogen and a metal catalyst, for example, a noble metal, for example, platinum, palladium or rhodium, which catalyst may be supported, for example, on charcoal or kieselguhr.

Alternatively, a p-nitrobenzyl ester may be converted to the free acid, by a two-step method, with an initial reduction of the nitro group, followed by hydrolysis. The nitro group may be reduced by chemical or catalytic reduction, for example, using a metal reducing agent, for example, zinc in acetic acid, aqueous tetrahydrofuran or acetone. The pH should be maintained within the range of from 3 to 6, preferably from 4 to 5.5, preferably by the use of aqueous hydrochloric acid. Other reducing agents are, for example, aluminum amalgam in a moist ether, for example, tetrahydrofuran, and iron and ammonium chloride in an aqueous ether, for example, aqueous tetrahydrofuran. Reduction of the nitro group is followed by hydrolysis which may occur in situ during reduction of the nitro group or which may be carried out subsequently by treatment with an acid or a base. An o-nitrobenzyl ester may be converted to the free acid by photolysis.

A stannyl ester, for example, a tri-n-butyl stannyl ester, may be split readily by hydrolysis, for example, by solvolysis, for example, using water, an alcohol, a pheno or a carboxylic acid, for example, acetic acid.

Certain ester groups may be split off by base hydrolysis, for example, acetylmethyl and acetoxymethyl ester groups.

There may be used an esterifying group that is removable under physiological conditions, that is to say, the esterifying group is split off in vivo to give the free acid or the carboxylate, for example, an acyloxymethyl ester, e.g. an acetoxymethyl or pivaloyloxymethyl ester, an aminoalkanyloxymethyl ester, for example, an L-glycyloxymethyl, L-valyloxymethyl or L-leucyloxymethyl ester, or a phthalidyl ester, or an optionally substituted 2-aminoethyl ester, for example, a 2-diethylamino-ethyl or 2-(1-morpholino)-ethyl ester.

Preferred esters are the p-nitrobenzyl, phthalidyl, pivaloyloxymethyl, acetylmethyl and acetoxy-methyl esters.

An ester of formula I, or of any other free acid described herein, may be prepared by reaction with an alcohol, phenol or stannanol or a reactive derivative thereof. The reaction is preferably carried out under mild conditions in order to prevent rupture of the ring or ring system, for example, under neutral or mild acidic or basic conditions, and at temperatures within the range of from $-70°$ to $+35°$ C.

An alkyl, alkoxyalkyl or aralkyl ester may be prepared by reaction of an acid of formula I or any other free acid with the appropriate diazoalkane or diazoaralkane for example, diazomethane or diphenyldiazomethane. The reaction is preferably carried out in an ether, ester or halogenohydrocarbon as solvent, for example, in diethyl ether, ethyl acetate or dichloromethane. In general, temperatures below room temperature are preferred, for example, from $-15°$ to $+15°$ C.

An ester derived from an alcohol may also be produced by reaction of a reactive derivative of the alcohol, for example, a halide, for example a chloride, bromide or iodide, or a hydrocarbonsulphonyl derivative, for example, a mesyl or tosyl ester, with a salt of an acid of formula I or another free acid described herein for example, an alkali or alkaline earth metal salt, for example, a lithium, sodium, potassium, calcium or barium salt or an amine salt, for example, a triethylammonium salt. This reaction is preferably carried out in a substituted sulphoxide or amide solvent for example, in dimethylsulphoxide, dimethylformamide or hexamethylphosphoramide or, alternatively, an ester may be prepared by reaction of the acid with the alcohol in the presence of a condensing agent, for example, dicyclohexylcarbodiimide.

A stannyl ester may be formed by reaction of a carboxylic acid of formula I or another free acid described herein, or a salt thereof with a reactive tetravalent tin compound, especially a trialkyl tin oxide.

The present invention also provides the salts of those compounds of formula I that have salt-forming groups, especially the salts of free acids of formula I and the acid addition salts of compounds of formula I having a basic group. The salts are especially physiologically tolerable salts, for example, alkali metal and alkaline earth metal salts, for example, sodium potassium, lithium, calcium and magnesium salts, ammonium salts and salts with an appropriate organic amine; also physiologically tolerable acid addition salts. These may be formed, with suitable inorganic and organic acids, for example, hydrochloric acid, sulphuric acid, carboxylic and organic sulphonic acids, for example, trifluoroacetic acid and p-toluene-sulphonic acid. Some compounds of formula I which contain a basic center may exist as Zwitterions; such salts are also part of this invention.

A salt of a free acid of formula I may be produced by reacting the free acid with the appropriate base in a solvent, preferably under conditions under which the salt precipitates. In the case of an alkali metal salt, for example, a sodium or potassium salt, the preferred base is an alkoxide.

A salt may be produced directly from an ester by splitting off the ester group under suitable reaction conditions, for example, catalytic reduction of an ester, for example, a p-nitrobenzyl ester, in an aqueous/organic solvent, for example, comprising water and ethyl acetate, dioxane, or tetrahydrofuran, in the presence of a metal salt, especially a bicarbonate, for example, in an equivalent amount or in a slight excess, yields a salt directly.

A compound of formula II may be prepared by a process which comprises (i) allowing a compound of the general formula III

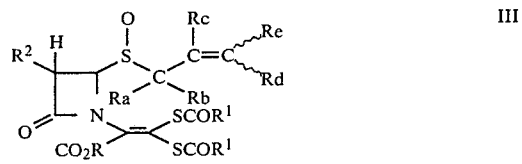

in which R and $R^2$ are as defined above, the two radicals $R^1$, which may be the same or different, are each as defined above for $R^1$, and in which Ra, Rb, Rc, Rd and Re, which may be the same or different, each represents a hydrogen atom, an alkyl or alkenyl group having up to 8 and preferably up to 4 carbon atoms, a cycloalkyl or cycloalkenyl group, a free or esterified carboxyl group, a halogen atom or a cyano group, and wherein any two of Ra to Re may form, together with the carbon atom or atoms to and through which they are attached, a cycloaliphatic ring containing from 3 to 10 carbon atoms, there being present zero, one or two of such rings, and wherein Rc is cis or trans to Rd and the group

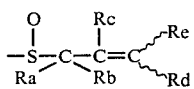

is cis or trans to $R^2$ to react with a trivalent organophosphorus compound to give a compound of formula II, or (ii) reacting a compound of the general formula IV

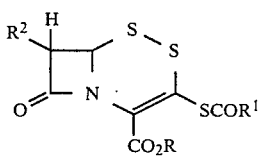

in which R, R$^1$ and R$^2$ are as defined above, with a trivalent organophosphorus compound.

A compound of formula IV is preferably produced by effecting ring closure in a compound of formula III as defined above.

Any of the interconversions (a) to (d) described above in relation to the compound of formula I may be carried out on a compound of formula II.

In the compound of formula III, the group

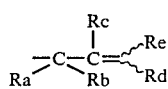

is preferably one of the following:

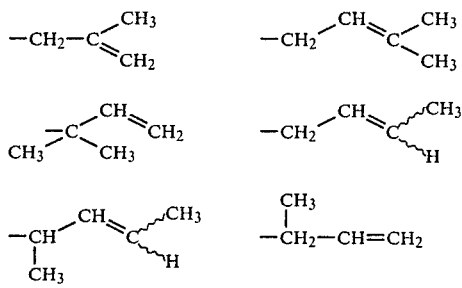

and especially the group —CH$_2$—CH=CH$_2$.

Ring closure of the compound of formula III occurs spontaneously at room temperature, but the reaction is generally carried out at a temperature within the range of from 20° to 150° C., preferably from 60° to 120° C., and generally under an inert gas atmosphere, for example, under an atmosphere of nitrogen or argon. The cyclization may be carried out in a solvent, which should be capable of achieving the desired temperature, for example, benzene toluene or dioxane.

The cyclization is preferably carried out in the presence of an acid, which reduces significantly the reaction time. The acid may be a protic inorganic acid, a protic organic acid, or a Lewis acid. Examples of protic inorganic acids are sulphuric acid and phosphoric acid.

A protic organic acid may be a carboxylic acid, for example, formic acid or acetic acid, or a derivative thereof, for example, chloroacetic acid, dichloroacetic acid or, especially, trifluoroacetic acid. Sulphonic acids are further example of organic acids which may be present during the cyclization of the compound of formula III. A sulphonic acid may be an alkyl sulphonic acid, for example, methanesulphonic acid or d- or l-camphor-10-sulphonic acid; or an aryl sulphonic acid, for example, benzenesulphonic acid, toluenesulphonic acid, benzenedisulphonic acid or a derivative thereof, for example, a chlorinated sulphonic acid.

A Lewis acid is, for example, boron trifluoride, boron trichloride, aluminium trichloride, titanium tetrachloride, tin tetrachloride, tin dichloride, zinc chloride and zinc bromide.

Preferred acids are boron trifluoride, in the form of an etherate e.g. boron trifluoride diethyl etherate, and toluenesulphonic acid. A preferred solvent is dioxane.

It is also preferable to carry out the cyclization in the presence of water, a lower alkanol, or a mixture of any two or more selected from water and lower alkanols. The water, lower alkanol, or mixture thereof is preferably used in an amount of from 1 to 20 equivalents, calculated on the compound of formula III. A lower alkanol is preferably methanol, ethanol or a propanol.

The water, lower alkanol or mixture thereof may be used either alone or in addition to the use of an acid.

It is thought that prior to cyclization, the compound of formula III re-arranges to the compound of formula IIIa

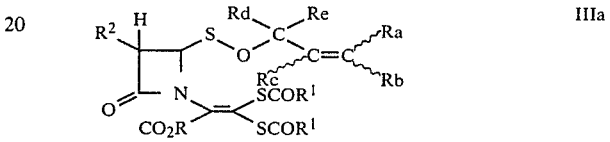

The compound of formula III may be cyclized to give compound IV, which is then treated with a trivalent organophosphorus compound, or the compound of formula III may be converted into the corresponding compound of formula II in one step. In the former case, the intermediate of formula IV may be isolated, or the treatment with the phosphine compound may be carried out in situ on the reaction mixture resulting from the cyclization step.

The trivalent organophosphorus compound is especially one of the general formula

PR$^6$R$^7$R$^8$ wherein R$^6$, R$^7$ or R$^8$, which may be the same or different, each represents an unsubstituted or substituted hydrocarbon group, for example, a straight or branched chain aliphatic group for example, alkyl group, an unsubstituted or substituted cycloaliphatic group for example cyclopentyl or cyclohexyl group, an unsubstituted or substituted aryl group for example, phenyl group; or an unsubstituted or substituted hydrocarbon group in which one or more carbon atoms are replaced by hetero atoms, especially nitrogen, oxygen and sulphur atoms, for example, alkoxy groups, amine groups, and aromatic and non-aromatic heterocyclic groups. Preferred tervalent organophosphorus compound are triphenylphosphine, tributylphosphine, trimethylphosphite and triethylphosphite.

A further preferred group of tervalent organophosphorus compounds are those in which, in PR$^6$R$^7$R$^8$ one or more of the groups R$^6$, R$^7$ and R$^8$ comprises an insoluble polymer, which aids removal after the reaction. Generally one polymeric substituent is adequate. (See, for example, H. M. Relles, and R. W. Schluenz, J. Amer. Chem. Soc. 96 6469, (1974) and S. L. Regen and D. P. Lee, J. Org. Chem. 40, (11), 1669, (1975).

Another preferred group of trivalent organophosphorus compounds are those in which, in PR$^6$R$^7$R$^8$, one or more of the groups R$^6$, R$^7$ and R$^8$ comprise a cationic or anionic center, for example, a quaternary ammonium group or a carboxylate or sulphate group. The presence of a charged group assists removal of the resulting organophosphorus sulphide, for example, by partition or by absorption on an insoluble ion exchange resin or by extraction into an aqueous solution at an appropriate pH, when the organophosphorus sulphide is water soluble.

The reaction of the compound of formula IV with the trivalent organophosphorus compound is preferably carried out in a dry, inert, aprotic organic solvent or diluent, for example, an ether or an ester, for example, diethylether, tetrahydrofuran or ethyl acetate; an aromatic hydrocarbon for example, benzene or toluene; a halogenated hydrocarbon, for example, methylene chloride or chloroform; or another organic solvent, for example, dimethylformamide or acetonitrile. Preferred solvents are methylene chloride and ethyl acetate. A mixture of two or more solvents or diluents may be used. The reaction may be carried out at a temperature of from 0° to 80° C., preferably from 0° to 20° C., and it is preferable to use at least 1 equivalent of the phosphorus compound per equivalent of the compound of formula IV.

The resulting compound of formula II may be isolated from the reaction mixture, for example, by chromatography or crystallisation. The compound of formula II may be obtained as a mixture of the 5R- and 5S-isomers. These isomers can be separated by known methods, if desired, or the compound of formula II can be used in the form of an isomeric mixture. The preferred stereochemistry in compound II is generally that of natural penicillins and cephalosporins i.e. 5R.

If R in formula II represents an esterifying group, this may be removed in the usual manner, depending on the nature of the ester group, for example, by hydrolysis, reduction, or enzymatically, to yield the free acid. A free acid or an ester may be converted into a salt, especially a physiologically tolerable salt, or a salt may be converted into another salt or the free acid or an ester. An ester may be transesterified, or a free acid converted into an ester, for example, to give an ester capable of removal under physiological conditions. Examples of such procedures are given above.

A compound of the general formula II may be produced in various ways, for example, as shown in the reaction scheme below, in which

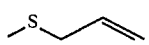

denotes the group

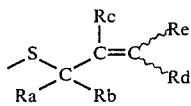

in which Ra to Re are as defined above.

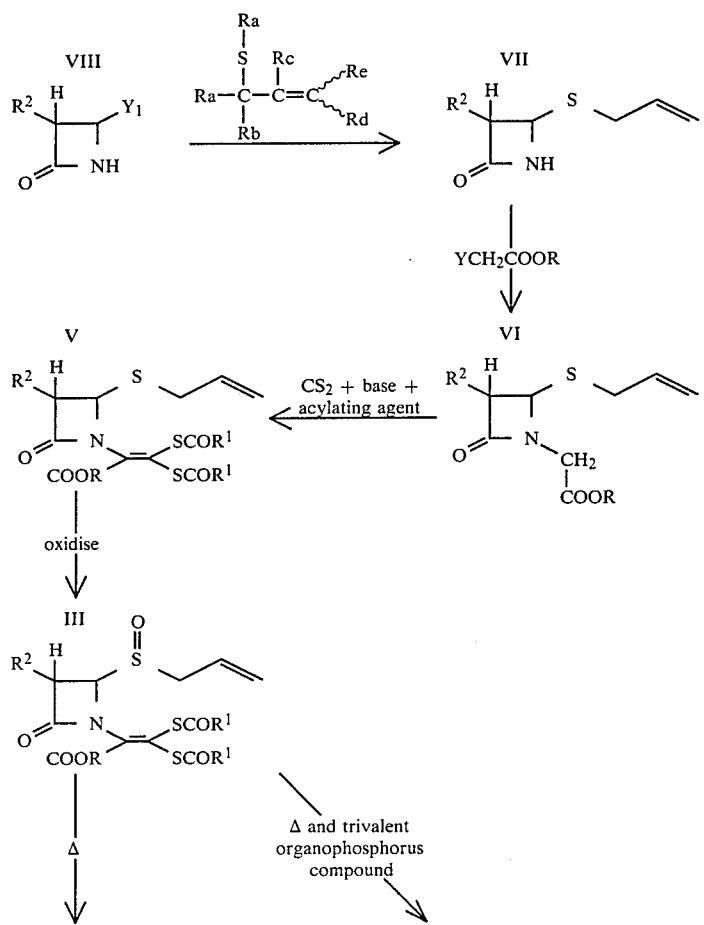

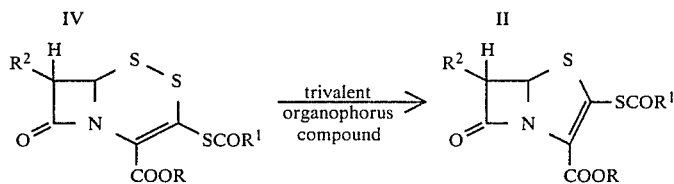

in which
R, R¹ and R² are as defined above,

Δ denotes that a reaction requires uptake of heat from an external source,

Y represents a group that is capable of being replaced by a nucleophilic group and is, for example, a halogen atom, for example, a chlorine, bromine or iodine atom, or a substituted, activated hydroxy group, for example, a sulphonyloxy group, for example, a radical of the formula

—OSO$_2$R$^9$ in which R$^9$ represents an aliphatic, cycloaliphatic, aryl or araliphatic group having up to 18 carbon atoms, which may be substituted or unsubstituted, for example, as described above for R². An aliphatic group R$^9$ is, for example, an alkyl group having up to 8 carbon atoms which may be substituted by one or more halogen atoms, for example, chlorine and bromine atoms. An aryl group R$^9$ has, for example, up to 15 carbon atoms, and may be substituted by one or more substituents, which may be the same or different, selected from alkyl and alkoxy groups, for example, methyl and methoxy groups, nitro groups, and halogen atoms, especially bromine atoms, R$^9$ preferably represents an unsubstituted or substituted aryl group having up to 18 carbon atoms, for example, a phenyl, p-tolyl, p-bromophenyl or p-nitrophenyl group, or an unsubstituted or substituted alkyl group, especially with 1 to 4 carbon atoms, and preferably a methyl or trifluoromethyl group.

Y preferably represents a bromine or iodine atom or a methylsulphonate, trifluoromethylsulphonate, tolylsulphonate or benzenesulphonate group.

Y$^1$ represents a group that is capable of being replaced by a nucleophilic group and is, for example, especially an activated hydroxy group, more especially, an acyloxy group, for example, an acetoxy group, or a sulphonyl group, for example, of the formula —SO$_2$R$_a^9$ in which R$_a^9$ represents an alkyl group having from 1 to 4 carbon atoms, an aryl group, for example, a phenyl group, or Y$^1$ represents a halogen atom, for example, a chlorine or bromine atom.

A compound of formula VIII may be prepared as described in, for example, Liebigs Annalen Chemie 1974, pp. 539–560, Claus, Grimm and Prossel; DT-OS No. 1 906 401; UK Specification No. 2 013 674; Japanese Published Application No. JA 80641; or H. R. Pfaendler, J. Gosteli and R. B. Woodward, J.A.C.S. 102:6 (1980), 2039–2043; Belgian Patent Specification No. 882.764. A compound of formula VIII may be converted into a compound of formula VII by reaction with a compound of formula

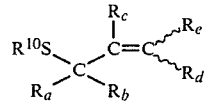

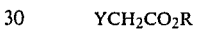

in which R$^{10}$ represents a hydrogen atom or an alkali metal atom especially a sodium or potassium atom, and Ra to Re are as defined above.

The reaction is generally carried out in a solvent, preferably a protic solvent, for example, water or an alcohol, or a non-protic, water-miscible solvent which is preferably polar, for example, dimethyl formamide, dimethyl sulphoxide, tetrahydrofuran or dioxane. The reaction temperature is, for example, from −20° to +100° C., preferably from −10° to +20° C.

A compound of formula VII may be reacted with a compound of formula IX

YCH$_2$CO$_2$R    IX in which Y and R are as defined above in the presence of a base, to give a compound of formula VI.

The base may be inorganic, organic or organometallic, for example, an alkali metal or alkaline earth metal hydroxide, oxide, carbonate, bicarbonate or hydride, for example, sodium hydroxide, magnesium oxide, potassium carbonate, potassium bicarbonate or sodium hydride; an amine, for example, a dialkylamine or trialkylamine, for example, triethylamine, dabco (diazabicyclo(2,2,2)octane), pyridine, or an alkyl-substituted or amino-substituted or dialkylamino-substituted pyridine for example, N,N-dimethylaminopyridine, or collidine; a guanidine, for example, tetramethylguanidine; DBN (diazabicyclononene) or DBU (diazabicycloundecene), a polymeric base i.e. a base attached to an inert polymeric support e.g. Hünig's base (diisopropylethylamine attached to polystyrene); a metallated amine, for example, a metallated alkyl or arylamine, for example, lithium diisopropylamide (LDA), lithium hexamethyldisilazide, lithium piperidide, lithium 2,2,6,6-tetramethylpiperidide, or a Grignard reagent. Preferred bases are, for example, potassium carbonate, sodium hydride, lithium diisopropylamide and triethylamine.

The reaction is generally carried out in a solvent or diluent that is inert under the reaction conditions, for example, an amide, for example, dimethylformamide, dimethylacetamide or hexamethylphosphoramide; a hydrocarbon, for example, benzene or toluene; an inert, aprotic solvent or diluent, for example, an ester, for example, ethyl acetate, or an ether, for example, diethylether, tetrahydrofuran or dioxane; or acetonitrile, nitromethane, dimethyl-sulphoxide, or sulpholane. Dimethylformamide and dimethylacetamide are preferred. A mixture of two or more solvents and/or diluents may be used.

The reaction may be carried out at a temperature within the range of from −80° C. to the reflux point of the reaction mixture, preferably from −40° to +50° C., and especially from −20° to +30° C.

From 1 to 1.5 moles of compound IX are preferably used per mole of compound VII, especially from 1 to 1.1 mole of IX per mole of VII. The base is used in an amount for example, from 1 to 4 moles of base per mole of compound VII.

The reaction is preferably carried out by dissolving compound VII in a solvent, advantageously in dimethylformamide with stirring, adding the base; adding the compound of formula IX and reacting at the desired temperature. The resulting compound of formula VI may be worked up and isolated in the usual manner, for example, using chromatographic and/or crystallisation techniques, or the subsequent reaction may be carried out directly on the resulting reaction mixture after removal of any solvent that is not compatible with the subsequent reaction.

If R in formula VI represents a carboxyl esterifying group, this group may be converted into another esterifying group R, for example, to introduce a group R that is more easily removable under desired conditions. This transesterification is generally carried out as follows: the ester of formula VI is hydrolysed in known manner using, for example, acid or alkaline hydrolysis, preferably an alkali metal hydroxide, especially sodium or potassium hydroxide. The ester of formula VI for example, a methyl ester, is preferably hydrolysed using an alkali metal hydroxide especially one mole thereof per mole of the ester of formula VI in a solvent, for example ethanol, methanol or water, or an aqueous-organic solvent, for example, tetrahydrofuran/water, ethanol/water, or acetonitrile/water.

The reaction mixture is then generally acidified, and the free acid is preferably isolated and, if desired, the free acid is then esterified with an esterifying agent capable of introducing a different esterifying group R, for example with an alcohol ROH in the presence of an acid or another activating agent, for example, dicyclohexylcarbodiimide, or with an alkylating agent RY in which Y is as defined above. Esterification methods are described above in relation to the compound of formula I.

Transesterification may be carried out on compound VI as described above, or on any other intermediate or on the final product of formula I.

As indicated in the reaction scheme above, compound VI may be converted to compound III by the addition of the group

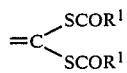

to the side chain attached to the nitrogen atom, followed by oxidation of the sulphur atom attached to position 3 of the azetidinone ring.

A compound of formula VI may be converted into a compound of formula V by treatment with a base in the presence of carbon disulphide followed by reaction with an acylating agent, or by treatment with a base, then with carbon disulphide, and finally reaction with an acylating agent. An acylating agent is generally an activated carboxylic acid.

The activated carboxylic acid may be any activated acid derivative comprising the group $R^1$. Such derivatives are well known in the art, and include acid chlorides, acid anhydrides, and activated esters.

An anhydride may be symmetrical or asymmetrical. An activated acid may comprise an unsubstituted or substituted carbonic, sulphonic or phosphoric ester group.

The acylating agent may have the general formula X $$R^1COZ \qquad \qquad X$$

in which Z represents a halogen atom, especially a chlorine atom, —$OCOR^{11}$ in which $R^{11}$ is as defined for $R^1$ and may be the same as $R^1$ or different, —$O_2COR^{12}$ or —$OSO_2R^{12}$, in which $R^{12}$ is as defined above for $R^9$,

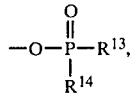

in which $R^{13}$ and $R^{14}$, which may be the same or different, each represents an unsubstituted or substituted alkyl, aryl or aralkyl group, or $R^{13}$ and $R^{14}$ together with the phosphorus atom may form a 5- or 6-membered ring, or either or both of $R^{13}$ and $R^{14}$ may represent a group —$OR_a^{13}$ or —$OR_a^{14}$ respectively, in which $R_a^{13}$ and $R_a^{14}$ are as defined above for $R^{13}$ and $R^{14}$ respectively and, in the case when $R^{13}$ represents —$OR_a^{13}$ and $R^{14}$ represents —$OR_a^{14}$, $R_a^{13}$ and $R_a^{14}$ may together represent a 5- or 6-membered ring.

The compound of formula VI is preferably reacted first with a base, then with carbon disulphide, and then finally with the acylating agent.

The base preferably has a pK ≧ 20, and is preferably a metallated amine. Examples of preferred bases are lithium diisopropylamide, lithium 2,2,6,6-tetramethylpiperidide, lithium cyclohexyl isopropylamide, lithium hexamethyl disilazide, and sodamide.

The reaction is generally carried out in an inert solvent, for example, an oxygenated hydrocarbon, preferably an ether, for example, diethyl ether, tetrahydrofuran, dioxane, glyme or diglyme. The reaction temperature is, for example, from −120° to +30° C., preferably from −100° to −20° C.

The amount of base used is for example, from 1 to 4 moles, calculated per mole of compound VI, preferably from 2.0 to 3.0 moles of base. Carbon disulphide is preferably used in an amount of from 1 to 5 moles, especially from 2 to 3 moles, per mole of compound VI.

The reaction is preferably carried out as follows: to a stirred solution of compound VI under an inert atomsphere is added the base then a solution of carbon disulphide in the same or a different solvent and finally the acylating agent to complete the reaction.

There may then be admixed a protic source having a pK less than 10, and especially from 5 to 2, for example, acetic, citric, oxalic or formic acid.

Oxidation of the resulting compound V may be carried out by any method capable of converting a sulphide into a sulphoxide, for example, there may be used an oxidising agent, for example, hydrogen peroxide, a periodate e.g. sodium periodate, ozone, a peracid e.g. peracetic acid or perbenzoic acid, a substituted perbenzoic acid e.g. m-chloroperbenzoic acid, or a permanganate salt, e.g. potassium permanganate. Preferred oxidising agents are hydrogen peroxide and m-chloroperbenzoic acid. Over oxidation should be avoided, for example, by using only one equivalent of a peracid.

The oxidation is preferably conducted in an inert solvent at a preferred temperature of from $-40°$ to $+30°$ C. Preferred solvents are ethyl acetate, methylene chloride, chloroform, acetonitrile, and lower alcohols, for example methanol and ethanol.

The resulting compound of formula III may be isolated and worked up using known methods.

It is advisable to esterify a free carboxyl group in a compound of formula III prior to cyclization. Although an ester group may be introduced immediately prior to cyclization, it is preferable to esterify the carboxyl group at an earlier stage in the preferred reaction sequence, for example, to esterify a free carboxyl group in a compound of formula V or VI to ensure that the carboxyl group does not take part in any of the subsequent reactions. An esterifying group may be transesterified to another ester group having more desirable properties for a particular stage of the reaction sequence.

Furthermore, it is advisable to protect any reactive moiety present in any of R, $R^1$ and $R^2$ so that such a moiety does not take part in any subsequent reaction. Examples of such moieties are hydroxy, carboxy and amine moieties. Groups suitable for protecting such reactive moieties are well known, as are methods for their removal. (cf Protective Groups in Organic Chemistry, editor J. F. W. McOmie, Plenum Press, 1973).

Examples of groups suitable for protecting hydroxyl moieties are tetrahydropyranyl groups, methoxyethoxymethyl groups, acyl groups, for example, acetyl, chloroacetyl and formyl groups, and silyl groups, for example, as described above for R, for example, trimethyl silyl and t-butyldimethylsilyl groups. Carboxy protecting groups are, for example, as described above for R. Amino protecting groups are, for example, t-butyloxycarbonyl, benzyloxycarbonyl, p-nitrobenzyloxycarbonyl, p-nitrobenzenesulphenyl and trityl groups.

Reactive moieties may be protected at any appropriate point in the reaction sequence, and the protective groups are preferably removed during or after the formation of the compound of formula I.

In a compound of formula II any one or more of the above steps (a), to (d) may be carried out, if appropriate, before conversion to a compound of formula I.

At each stage of the preferred reaction sequence, the desired compound may be isolated from the reaction mixture and, if desired, purified by appropriate techniques generally used for the purification of organic compounds, for example, chromatography or crystallisation.

As indicated above, various intermediates may be produced in the form of mixtures of isomers of various kinds. Such a mixture may be separated or resolved at any stage, or the isomeric mixture may be used per se for subsequent reactions.

All of the compounds that are provided by the invention may exist in any appropriate isomeric form, as discussed above, either as a pure isomer or as a mixture of any two or more isomers.

A compound of the general formula I may exist in the tautomeric forms of formulae Ia and Ib, and each of these forms may have the R or S stereochemistry independently at positions 5 and 6 and also, in formula Ia, at position 2. Further isomeric forms will occur when any substituent contains a chiral atom. Any mixture of any two or more isomeric forms may be resolved, if desired, and/or an isomeric mixture may be prepared.

The compounds of the general formula I are particularly useful in the synthesis of substituted penems. For this purpose the compound of formula I are reacted in an inert solvent in the presence of an excess of a base, preferably 1 to 2 equivalents and an excess of an alkylating agent, preferably 1 to 3 equivalents.

Preferred bases are organic bases such as secondary or tertiary alkylamines, e.g. triethylamine, diisopropylamine, methyl-diisopropylamine or inorganic bases such as $Na_2CO_3$, $K_2CO_3$, $NaHCO_3$. Preferred alkylating agents are alkyl halides preferably brominated or iodinated lower alkyls.

The reaction is carried out in an appropriate solvent such as tetrahydrofuran, dioxane, ethylacetate, methylene chloride, chloroform, dimethylformamide.

The preferred reaction temperature is 0° to 40° C.

The compounds of formula I and salts thereof are $\beta$-lactamase inhibitors, and the compounds are generally stable to the action of $\beta$-lactamases produced by gram positive organisms, for example, by *Staphylococcus aureus* and gram negative organisms, for example, Enterobactercloacae. They also posses antibacterial properties themselves and may be used in humans and other animals, for example, to treat bacterial infections caused by gram positive and gram negative bacteria, for example, *Staphylococcus aureus, Streptomyces pyogenes, Bacillus subtilis, E. coli, Pseudomonas aeruginosa,* and *Proteus inorganii,* some strains of which are pencillin-resistant.

The invention accordingly provides a pharmaceutical preparation which comprises a compound of formula I or a physiologically tolerable salt of a compound of formula I or a mixture of two or more such substances, as active ingredient, in admixture or conjunction with a pharmaceutically suitable carrier. The preparation may also comprise one or more other pharmaceutically active substances, for example, another antibacterial substance, especially one which has a $\beta$-lactam ring. The preparation may be in a form suitable for enteral or parenteral administration, for example, for oral, intravenous, or intramuscular administration, for example, as tablets, capsules, syrups, or sterile injectable or infusible solutions. The preparations are advantageously in unit dosage form and preferably comprise from 10 to 200 mg of the active ingredient. The daily dosage of the active substance is generally from 20 to 8000 mg, in divided doses, generally up to 4 doses.

The invention also provides the use of an active compound as defined above as a $\beta$-lactamase inhibitor and/or as an antibacterial agent.

The invention further provides a pharmaceutical preparation which comprises an active compound as defined above, or a physiologically tolerable salt thereof, or a mixture of two or more such substances, in unit dosage form.

The invention also provides a pharmaceutical preparation which comprises an active compound as defined above, or a physiologically tolerable salt thereof or a mixture of two or more such substances, and one or more further pharmaceutically active substances, for example, as described above and, for example, in unit dosage form.

Unit dosages are preferably as described above.

The following Examples illustrate the invention. In them, temperatures are expressed in degrees Celsius.

EXAMPLE 1

4-Allylthioazetidin-2-one

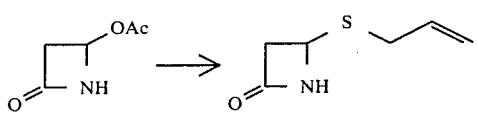

A solution of 42.9 g of sodium hydroxide in 500 ml of water was made up under nitrogen and cooled to room temperature, 108 ml of allyl mercaptan were added and the mixture stirred under nitrogen for 30 minutes. 138.7 g of 4-acetoxyazetidin-2-one were added to the mixture over 10 minutes under nitrogen and the reaction mixture was stirred overnight. The reaction was checked for completion by T.L.C. (hexane-ethyl acetate) and extracted into dichloromethane (6×250 ml). The organic layer was washed with water (2×250 ml), dried over magnesium sulphate and evaporated in vacuo to dryness. Purification, over silica gel and elution with hexane-ethyl acetate afforded the above product as a yellow oil. (112.1 g, 73% of the theoretical yield). $\nu max = 1769, 1778$ (sh) cm$^{-1}$.

$\delta$(CDCl$_3$) 2.86 (1H, ddd, $J_{NH,3\beta}$1.5 Hz, $J_{4,3\beta}$3 Hz, $J_{3\alpha,3\beta}$15 Hz, 3$\beta$-H) 3.28 (2H, d, J 7 Hz, S—CH$_2$), 3.37 (1H, ddd, $J_{NH,3\alpha}$1.5 Hz, $J_{4,3\alpha}$6 Hz, $J_{3\beta,3\alpha}$15 Hz, 6$\alpha$-H), 4.71 (1H, dd, $J_{3\beta,4}$3 Hz, $J_{3\alpha,4}$6 Hz, 4-H), 4.93–5.38 (2H, m, =CH$_2$), 5.49–6.24 (1H, m, CH=), 7.43 (1H, bs, NH). m/e 143.0405 (M+).

EXAMPLE 2

4'-Nitrobenzyl 2-(4-allylthioazetidin-2-on-1-yl)acetate

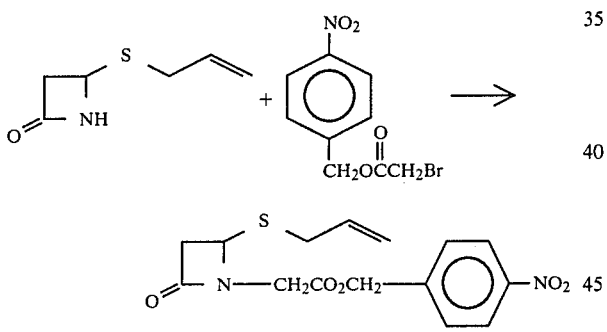

11.5 g of 4-nitrobenzylbromoacetate in 30 ml of dimethylformamide were added to 5.0 g of 4-allylthioazetidin-2-one dissolved in 70 ml of dimethylformamide with stirring under argon at room temperature. After 5 mins, 10.61 g of potassium carbonate were added to the solution. During the following 20 mins there was a color change in the mixture from yellow to dark brown. Stirring was continued for a further 3 hrs 40 mins when TLC analysis indicated completion of reaction. The mixture was poured into water (300 ml), extracted into ethyl acetate (4×100 ml) and the combined organic extracts washed with water (3×200 ml). The organic layer was dried with MgSO$_4$ and evaporated to leave a yellow oil.

The crude product was chromatographed on silica gel using ethyl acetate/hexane mixtures as eluant. 5.89 g of product was obtained (50% of the theoretical yield). $\delta$(CDCl$_3$) 3.05 (1H,2d,J trans 3 Hz,3-H), 3.17 (1H,S,S-CH$_2$—).

3.30 (1H,S, S—CH$_2$), 3.53 (1H,2d,J cis 5 Hz,J gem 15 Hz, 3-H), 3.84 and 4.38 (2H,ABq,J18 Hz,—N—CH$_2$—), 4.95 (1H,2d,4-H), 5.00–5,34 (2H,m, =CH$_2$), 5.34 (2H,S,—O—CH$_2$), 5.54–6.40 (1H,m, =CH), 7.53–8.38 (4H,m,—C$_6$H$_4$)

$\nu max$ (CDCl$_3$) 1769,1758 cm$^{-1}$ m/e 336.0525 (M+), 295.0391 (M—CH$_2$CHCH$_2$), 136.0385 (base peak)

EXAMPLE 3

Methyl 2-(4-allylthioazetidin-2-on-1-yl)acetate

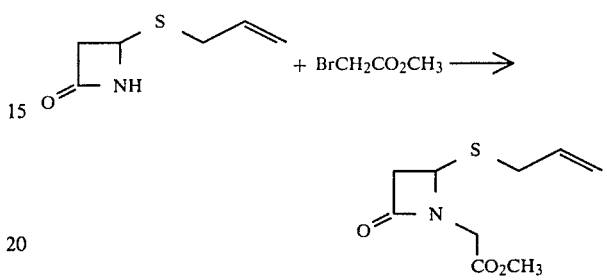

21.8 ml of methyl bromoacetate in 220 ml of dimethylformamide were added to 31.1 g of 4-allylthioazetidin-2-one dissolved in 420 ml of dimethylformamide, with stirring, under argon, at room temperature. After 5 mins, 66.0 g of anhydrous potassium carbonate were added to the solution. The suspension was then stirred for a further 18 hours.

The mixture was poured into water (2.5 l), extracted into ethyl acetate (3×1200 ml) and washed with water (3×2 l). The organic layer was dried with MgSO$_4$ and evaporated to leave a yellow oil.

The crude product was chromatographed on silica gel using ethyl acetate/hexane mixtures as eluant, 22.0 g of the above product was obtained. (47% of the theoretical yield)

$\delta$(CDCl$_3$) 2.97 (1H,2d,J trans 3 Hz,3-H), 3.16 (1H,S,S—CH$_2$—), 3.26 (1H,S, S—CH$_2$—), 3.45 (1H,2s,J cis 5 Hz,J gem 15 Hz, 3-H), 3.66 and 4.23 (2H,ABq,J 17 Hz,—N—CH$_2$—), 3.72 3H,S,CH$_3$), 4.86 (1H,2d,4-H), 4.95–5.27 (2H,m, =CH$_2$), 5.50–6.15 (1H,m, =CH)

$\nu_{max}$ (CHCl$_3$) 1766, 1749 cm$^{-1}$ m/e 215,0539 (M+), 142.0456 (base peak)

EXAMPLE 4

Methyl 2-(4-allylthioazetidin-2-on-1-yl)acetate

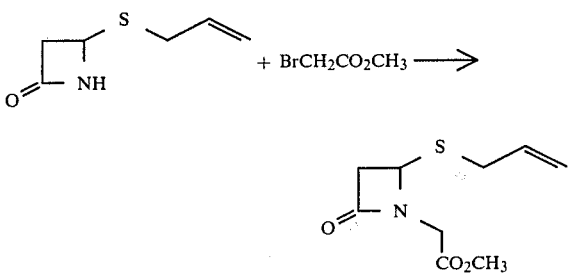

0.070 ml of methylbromoacetate in 1 ml of dimethylformamide was added to 0.100 g of 4-allylthioazetidin-2-one dissolved in 2 ml of dimethylformamide with stirring under argon at 0°. After 5 mins, 0.040 g of hexane washed sodium hydride, was added to the solution. The cooling bath was removed and stirring continued for a further 45 mins, when TLC analysis indicated completion of reaction.

The mixture was poured into water (15 ml), extracted into ethyl acetate (2×12 ml) and washed with water (3×15 ml). The organic layer was dried with MgSO₄ and evaporated to leave a yellow oil.

Yield: 0.089 g, (59% of the theoretical yield). (For spectral data see Example 3)

EXAMPLE 3

2-(4-Allylthioazetidin-2-on-1-yl)acetic acid

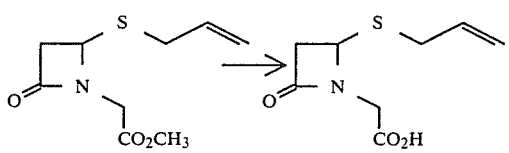

2.34 g of potassium hydroxide dissolved in a mixture of 285 ml of ethanol and 15 ml of water were added to 6.0 g of methyl 2-(4-allylthioazetidin-2-on-1-yl)acetate with stirring at room temperature. The solution was poured into 720 ml 1M hydrochloric acid, extracted into dichloromethane (2.650 ml), the organic layer extracted with saturated sodium bicarbonate solution and the aqueous phase acidified to pH1 with 5M hydrochloric acid. This solution was extracted into dichloromethane (5×650 ml), dried with MgSO₄ and evaporated to leave a colorless oil.

Yield: 5.37 g (96%)

$\delta(CDCl_3)$ 3.06 (1H,2d,J trans 3 Hz,3-H), 3.19 (1H,S, S—CH₂—), 3.30 (1H,S,S—CH₂), 3.53 (1H,2d,J cis 5 Hz,J gem 16 Hz,3-H), 3.75 and 4.36 (2H,ABq,J18 Hz,N—CH₂—), 4.96 (1H,2d,4-H), 5.03-5.34 (2H,m, =CH₂), 5.58-626 (1H,m,H—C=)

$\nu_{max}$ (CDCl₃) 1765, 1730 cm⁻¹ m/e 201.0500 (M+), 86.0239 (base peak).

EXAMPLE 6

Pivaloyloxymethyl 2-(4-allylthioazetidin-2-on-1-yl)-2-acetate

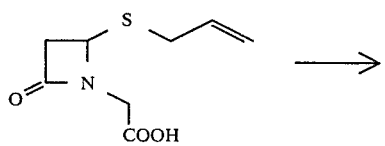

To a solution of 14 mls of diisopropylamine and 20.4 g of 2-(4-allylthioazetidin-2-on-1-yl) acid in 450 ml of dimethylformamide, at 0° C., were added dropwise 14 ml of chloromethylpivalate. The solution was warmed to room temperature and stirred for 5 days until TLC analysis (silica gel: hexane-ethyl acetate) showed absence of starting material. The reaction mixture was poured into water (500 ml), and extracted into ethyl acetate (3×500 ml); the organic layer was washed with hydrochloric acid (pH 2.0, 400 ml), then water (2×500 ml), dried over magnesium sulphate and evaporated to dryness. The crude product was purified over silica gel eluting with hexane/ethyl acetate to give the above product as a pale yellow oil (20.1 g, 63%).

$\nu_{max}$=1760, 1768, 1776 cm⁻¹

$\delta(CDCl_3)$ 1.20 (9H, s. C(CH₃)₃), 2.99 (1H, dd, $J_{4,3\beta}$ 3 Hz $J_{3\alpha,3\beta}$ 16 Hz, 3β-H), 3.27 (2H, d, J 7 Hz, S—CH$_z$), 3.53 (1H, dd, $J_{4,3\alpha}$ 5 Hz, $J_{3\beta,3\alpha}$ 16 Hz, 3α -H), 4.08 (2H, q, J 18 Hz, N—CH₂), 4.93 (1H, dd, $J_{3\alpha,4}$ 5 Hz, $J_{3\beta,4}$ 3 Hz, 4-H), 5.03-5.50 (2H,m, =CH₂), 5.57-6.23 (1H, m, CH=), 6.80 (2H,3,CO₂CH₂)

EXAMPLE 7

Methyl 3,3-di(acetylthio)-2-(4-allylthioazetidin-2-on-1-yl)propenoate

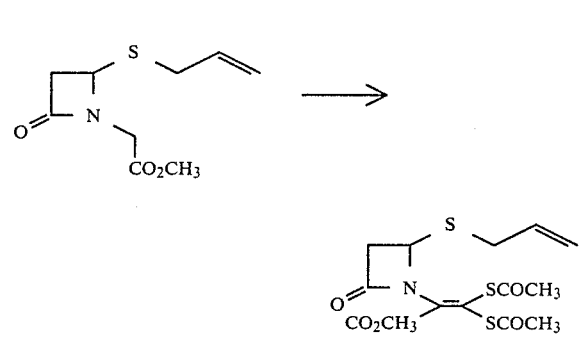

EXAMPLE 7a

A solution of lithium hexamethyldisilazide was prepared by the addition of 5.12 ml of a 1.6M solution of n-butyllithium in hexane to 1.75 ml of hexamethyldisilazane in 25 ml of dry THF at −10° with stirring, under argon. The solution was cooled to −78° and added to 1.0 g of methyl 2-(4-allylthioazetidin-2-on-1-yl)acetate in 12 ml of dry tetrahydrofuran at −78°, with stirring, under argon. After 5 min, 0.846 ml of carbon disulphide was added by syringe. 1.77 ml of acetic anhydride were then added, followed by 1.07 ml of glacial acetic acid. The solution was allowed to warm to room temperature and evaporated to leave a yellow oil.

The crude product was chromatographed on silica gel using ethyl acetate/hexane mixtures as eluant. 1.14 g (66%) of the above product was obtained.

$\delta(CDCl_3)$ 2.38 (6H,S, $$-\overset{O}{\underset{\|}{C}}-CH_3),$$

3.17 (1H, 2d, J trans 3Hz, 3-H), 3.35 (1H,S,S—CH₂—), 3.45 (1H,S, S—CH₂—), 3.43-3.78 (1H,2d,J gem 15 Hz, 3-H), 3.86 (3H,S,—O—CH₃), 5.06-5.45 (3H,m,=CH₂,4-H), 5.63-638 (1H,m,=CH)

$\nu_{max}$1786, 1740, 1715 cm⁻¹ m/e 157(O=C—N C—S CO₂CH₃ ),

127( S—CH₂ ), 73(S ),

43(COCH₃) (base peak)

EXAMPLE 7b

A solution of lithium hexamethyldisilazide was prepared by the addition of 32.9 ml of a 1.6M solution of n-butyllithium in hexane to 11.25 ml of hexamethyldisilazane in 125 ml of dry THF at −10° with stirring, under argon. The solution was cooled to −78° and added to 5.0 g of methyl 2-(4-allylthioazetidin-2-on-1-yl)acetate in 60 ml of dry tetrahydrofuran at −78°, with stirring, under argon. After 5 min, 4.23 ml of carbon disulphide was added by syringe. 885 ml of acetic anhydride was then added. The solution were allowed to warm to room temperature and evaporated to leave a yellow oil.

The crude product was purified by extraction using chloroform and water, and the resulting organic phase was evaporated to give a yellow oil, having the characteristics given in Example 7a.

EXAMPLE 8

Methyl 3,3-di(acetylthio)2-(4-allylsulphinylazetidin-2-on-1-yl)propenoate

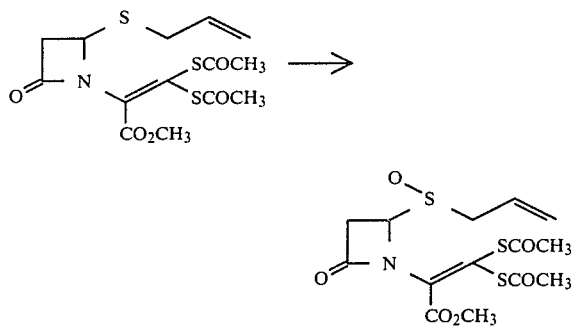

EXAMPLE 8a 0.549 g of 3-chloroperbenzoic acid (81% pure) in 7 ml of ethyl acetate (7 ml) was added dropwise over 20 mins to a stirred solution of 0.939 g of methyl 3,3-di(acetylthio)-2-(4-allylthioazetidin-2-on-1-yl)propenoate in 18 ml of ethyl acetate at −35° C. The solution was evaporated to dryness, slurried with dichloromethane and chromatographed on silica gel using ethyl acetate/hexane mixtures as eluant. 0.659 g (67%) of the above product was obtained.

δ(CDCl$_3$) 2.38 (3H,S—C—CH$_3$), 2.42 (3H,S—C—CH$_3$) 3.06–3.70 (4H,m,3-H,S—CH$_2$—), 3.87 (3H,S,—O—CH$_3$), 5.24–6.55 (4H,m,HC=CH$_2$, 4-H).

ν$_{max}$(CDCl$_3$) 1796, 1730 cm$^{-1}$

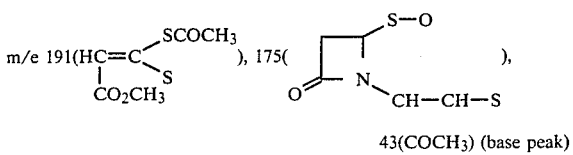

43(COCH$_3$) (base peak)

EXAMPLE 8b 5.50 g of 3-chloroperbenzoic acid in 30 ml of ethyl acetate were added dropwise over 30 mins to a stirred solution of the methyl 3,3-di(acetylthio-2-(4-allylthioazetidin-2-on-1-yl)propenoate obtained in Example 7b, in 50 ml of ethyl acetate at −35° C. The solution was evaporated to dryness, slurried with dichloromethane and chromatographed on silica gel using ethyl acetate/hexane mixtures as eluant. 6.26 g of the title product were obtained. (69% of the theoretical yield, calculated on the starting material of Example 7b. Analytical data as in Example 8a).

EXAMPLE 9

Methyl 3-acetylthio-8-oxo-4,5-dithia-1-azabicyclo[4,2,0]oct-2-ene-2-carboxylate

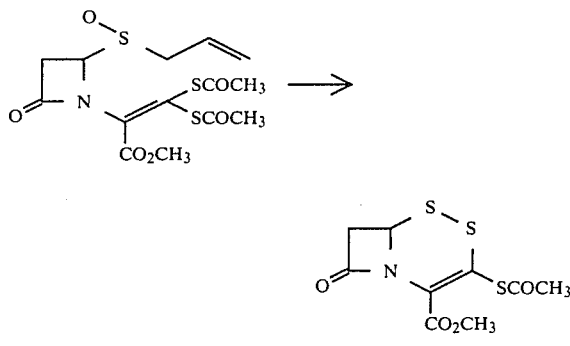

EXAMPLE 9a 0.050 g of methyl 3,3-di(acetylthio)-2-(4-allylsulphinylazetidin-2-on-1-yl)propenoate was refluxed in 5 ml of dioxane until TLC analysis indicated complete consumption of starting material (3 hrs). The crude product was chromatographed on silica gel using ethyl acetate/hexane mixtures as eluant. 0.009 g (24%) of the above product was obtained.

δ(CDCl$_3$) 2.44 (3H,S,

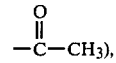

3.15 (1H,2d,J trans 3 Hz, 7-H), 3.88 (1H,2d,J cis 5 Hz,J gem 17 Hz,7-H), 3.90(3H,S,—O—CH$_3$), 4.89 (1H,2d,6-H)

ν$_{max}$ (CDCl$_3$) 1794, 1739 cm$^{-1}$ m/e 290.9743 (M+), 43.0211 (base peak).

EXAMPLE 9b 0.250 g of methyl 3,3-di(acetylthio)-2-(4-allylsulphinylazetidin-2-on-1-yl)propenoate and 80.2 μl of boron trifluoride diethyl etherate were refluxed in 12 ml of dioxan for 40 minutes, when TLC analysis indicated complete consumption of starting material. The crude product was evaporated to dryness and chromatographed on silica gel using ethyl acetate/hexane mixtures as eluant. 0.090 g (48%) of the title product was obtained.

EXAMPLE 9c 0.500 g of methyl 3,3-di(acetylthio)-2-(4-allylsulphinylazetidin-2-on-1-yl)-propenoate and 0.242 g of 4-toluenesulphonic acid hydrate were heated under reflux in 25 ml of dioxan for 40 minutes, when TLC analysis indicated complete consumption of the starting material. Purification of the crude product was carried out as described in Example 9b. 0.120 g (32%), of the purified product was obtained.

EXAMPLE 9d

The procedure described in Example 9c was carried out, substituting 0.30 ml of trifluoroacetic acid for the 0.242 g of 4-toluenesulphonic acid hydrate, and refluxing for 2 hours. 0.064 g of purified product was obtained (17% of the theoretical yield).

EXAMPLE 10

Methyl 3-acetylthio-7-oxo-4-thia-1-azabicyclo[3,2,0]hept-2-ene-2-carboxylate

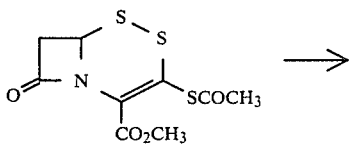

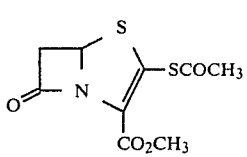

0.064 g of methyl 3-acetylthio-8-oxo-4,5-dithia-1-azabicyclo[4,2,0]oct-2-ene-2-carboxylate was dissolved in 1 ml of deuterochloroform and 0.063 g of triphenylphosphine added. TLC and NMR analysis indicated complete conversion of starting material to product. The crude product was chromatographed on silica gel using ethyl acetate/hexane as eluant to give 0.035 g (61%) of purified product.

$\delta$(CDCl$_3$) 2.47 (3H,S,

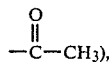

3.15–4.05 (5H,m,J trans 2 Hz, J$_{cis}$ 4 Hz, J$_{gem}$ 17 Hz, —O—CH$_3$, 6-H), 3.85 (3H,S,—O—CH$_3$), 5.73 (1H,2d,5-H)

$\nu_{max}$ (CDCl$_3$) 1798, 1710 cm$^{-1}$ m/e 258.9970 (M+), 174.9745 (base peak)

EXAMPLE 11

Pivaloyloxymethyl 3,3-di(acetylthio)-2-(4-allylthioazetidin-2-on-1-yl)propenoate

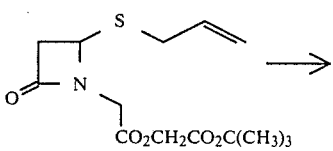

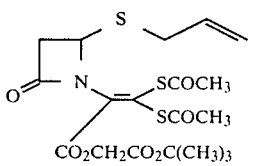

A solution of lithium hexamethyldisilazide was prepared by the addition of 3.53 ml of a 1.6M solution of n-butyllithium in hexane to 1.19 ml of hexamethyldisilazane in 25 ml of dry tetrahydrofuran at −10° with stirring under argon. The solution was cooled to −78° and added by cannula to 1.02 g of pivaloyloxymethyl 2-(4-allylthioazetidin-2-on-1-yl)acetate in 10 ml of dry tetrahydrofuran at −78° with stirring under argon.

After 5 minutes 582 μl of carbon disulphide were added by syringe. After 15 minutes, 1.22 ml of acetic anhydride was added followed by 0.74 ml of glacial acetic acid. The solution were allowed to warm to room temperature and the tetrahydrofuran solvent was removed by evaporation to leave an oily residue.

The crude product was chromatographed on silica gel using ethyl acetate/hexane mixtures as eluant. 0.755 g (49%) of purified product was obtained.

$\delta$(CDCl$_3$) 1.25 (9H,S, C(CH$_3$)$_3$), 2.28

3.0–3.7 (4H,m,3-H and S—CH$_2$—), 5.0–6.1 (6H,m,4-H and —CH=CH$_2$ and O—CH$_2$—)

$\nu_{max}$ (CDCl$_3$) 1784, 1758, 1746(sh), 1720(sh) cm$^{-1}$

EXAMPLE 12

Pivaloyloxymethyl 3,3-di(acetylthio)-2-(4-allylsulphinylazetin-2-on-1-yl)propenoate

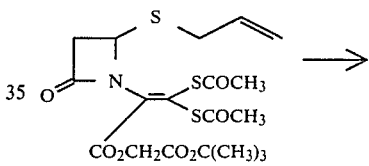

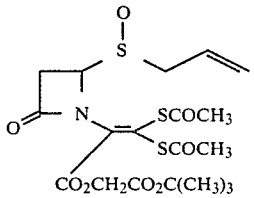

363 mg of 3-chloroperbenzoic acid in 3 ml of ethyl acetate were added portionwise to a stirred solution of 673 mg of pivaloyloxymethyl 3,3-di(acetylthio)-2-(4-allylthioazetidin-2-on-1-yl)propenoate in 10 ml of ethyl acetate. The solution was then allowed to warm to room temperature, evaporated to dryness and chromatographed on silica gel using ethyl acetate/hexane mixtures as eluant. The product was obtained as a mixture of R and S sulphoxides which were partially separated during the chromatography. Total yield of product, a yellow oil, was 0.502 g (72%).

$\delta$(CDCl$_3$) 1.24 (9H,S,CMe$_3$), 2.42

3.0–4.0 (4H,m,3-H and S—CH$_2$—), 5.2–61. (6H,m,4-H and —CH=CH$_2$ and O—CH$_2$—)

$\nu_{max}$ (CDCl$_3$) 1791, 1750 cm$^{-1}$

EXAMPLE 13

Pivaloyloxymethyl 3-acetylthio-8-oxo-4,5-dithia-1-azabicyclo[4,2,0]oct-2-ene-2-carboxylate

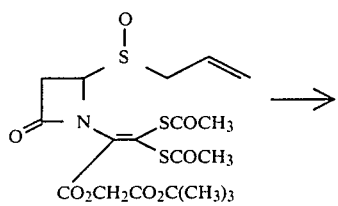

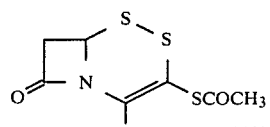

A solution of 82 mg of pivaloyloxymethyl 3,3-di(acetylthio)-2-(4-allylsulphinylazetidin-2-on-1-yl)propenoate and 32 mg of 4-toluenesulphonic acid hydrate in 10 ml of dioxan was heated rapidly to reflux and maintained under reflux for 1 hour. The solvent was removed by evaporation and the residue chromatographed on silica gel using ethyl acetate/hexane mixtures as eluant. The product (35 mg, 54%) was obtained as a yellow oil.

δ(CDCl$_3$) 1.25 (9H,S,C(CH$_3$)$_3$), 1.61

(3H,S,—$\overset{\overset{\text{O}}{\|}}{\text{C}}$CH$_3$), 3.1 (1H,2d,J$_{trans}$ 3 Hz, 7-H), 3.88 (1H,2d,J$_{cis}$5Hz, J$_{gem}$ 16 Hz, 7-H), 5.87 (2H,S,—OCH$_2$—), 4.83 (1H,2d,6-H).
ν(CDCl$_3$) 1796, 1757 cm$^{-1}$

EXAMPLE 14

Pivaloyloxymethyl 3-acetylthio-7-oxo-4-thia-1-azabicyclo[3,2,0]hept-2-ene-2-carboxylate

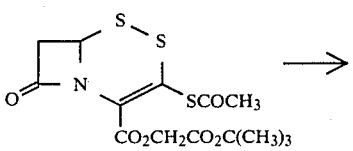

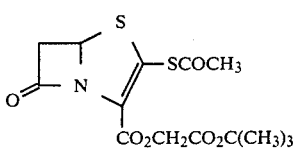

To a solution of 22 mg of pivaloyloxymethyl 3-acetylthio-8-oxo-4,5-dithia-1-azabicyclo[4,2,0]oct-2-ene-2-carboxylate in deuterochloroform were added 14.7 mg of triphenylphosphine. TLC analysis indicated complete conversion of the starting material and the product was shown by IR and NMR analysis to be the title compound. This product was isolated by chromatography on silica gel using ethyl acetate/hexane mixtures as solvent. The yield of product was 13 mg (65%).

δ(CDCl$_3$) 1.22 (9H,S, —C(CH$_3$)$_3$), 2,47 (3H,S,

3.5 (1H,2d,J$_{trans}$ 2 Hz, 6-H), 3.9 (1H,2d,J$_{cis}$ 4 Hz, J$_{gem}$ 17 Hz, 5.7 (1H,2d,5-H) 5.9 (2H,S,—CH$_2$O—).
ν(CHCl$_3$) 1801, 1750, 1719 cm$^{-1}$

EXAMPLE 15

4-Nitrobenzyl 3,3-di(acetylthio)-2-(4-allylthio-azetidin-2-on-1-yl)propenoate

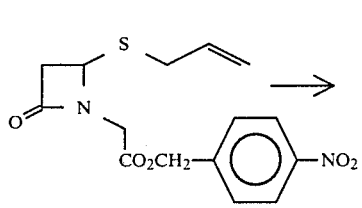

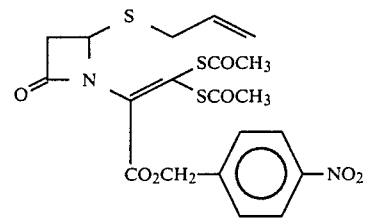

EXAMPLE 15a

A solution of lithium hexamethyldisilazide was prepared by the addition of 5.12 ml of a 1.6M solution of n-butyllithium in hexane to 1.75 ml of hexamethyldisilazane in 25 ml of dry THF at −10° with stirring, under argon. The solution was cooled to −78° and added by cannula to 1.57 g of 4-nitrobenzyl 2-(4-allylthioazetidin-2-on-1-yl)acetate in 12 ml of dry THF at −78°, with stirring under argon. After 5 minutes 0.846 ml of carbon-disulphide was added by syringe. 1.77 ml of acetic anhydride were then added, followed by 1.07 ml of glacial acetic acid. The solution was allowed to warm to room temperature and evaporated to leave an orange oil.

The crude product was chromatographed on silica gel using dichloromethane/hexane mixtures as eluant. 0.541 g (23%) of pure product was obtained.

δ(CDCl$_3$) 2.26 (3H,S, —C—CH$_3$), 2.38 (3H,S, $-\overset{\overset{\text{O}}{\|}}{\text{C}}-\text{CH}_3$)

3.00–3.72 (4H,m,3-H, S—CH$_2$—) 5.01–6.44 (6H,m, HC═CH$_2$, —O—CH$_2$, 4-H) 7.33–8.34 (4H,m, C$_6$H$_4$)
ν$_{max}$ (CDCl$_3$) 1785, 1742, 1716 cm$^{-1}$ m/e 354(O═C—N—C<$\begin{smallmatrix}\text{SCOCH}_3\\\text{SH}\\\text{COOCH}_2\text{C}_6\text{H}_4\text{NO}_2\end{smallmatrix}$), 73(S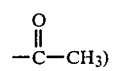), 43(COCH$_3$) (base peak)

EXAMPLE 15b

A solution of lithium hexamethyldisilazide was prepared by the addition of 8.66 ml of a 1.6M solution of n-butyllithium in hexane to 2.96 ml of hexamethyldisilazane in 30 ml of dry THF at −10° with stirring under argon. The solution was cooled to −78° and added by cannula to 2.07 g of 4-nitrobenzyl 2-(4-allylthioazetidin-2-on-1-yl)acetate in 15 ml of dry THF at −78°, with stirring, under argon. After 5 minutes 1.11 ml of carbon disulphide were added by syringe. 2.33 ml of acetic anhydride were then added. The solution was allowed to warm to room temperature and evaporated to give an orange oil. The oil was mixed with water (40 ml) and chloroform (40 ml), the organic layer separated and the aqueous layer extracted with additional chloroform (2×40 ml). The combined organic phase was dried (MgSO$_4$) and evaporated to give an orange oil, which was used without further purification as the starting material for Example 16b.

EXAMPLE 16
4-Nitrobenzyl 3,3-di(acetylthio)-2-(4-allylsulphinylazetidin-2-on-1-yl)propenoate

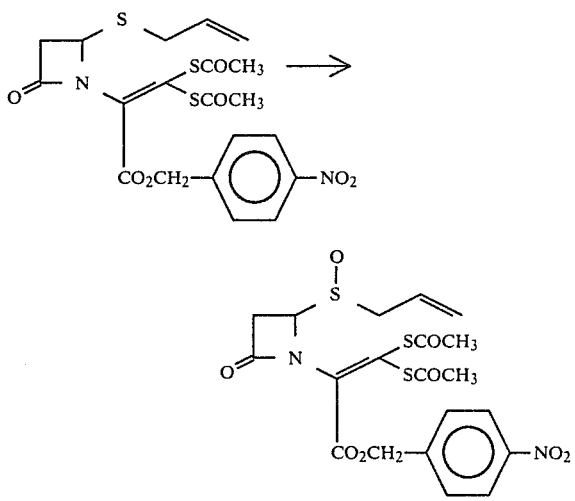

EXAMPLE 16a 0.241 g of 3-chloroperbenzoic acid (81% pure) in 5 ml of ethyl acetate was added dropwise over 20 minutes to a stirred solution of 0.534 g of 4-nitrobenzyl 3,3-di(acetylthio)-2-(4-allylthioazetidin-2-on-1-yl)propenoate in 10 ml of ethyl acetate at −35°. When TLC analysis indicated almost complete conversion of the starting material to product, the solution was evaporated to dryness, slurried with dichloromethane and chromatographed on silica gel using ethyl acetate/hexane mixtures as eluant. 0.310 g (56%) of purified product was obtained.

δ(CDCl$_3$) 2.26 (3H,S, —C—CH$_3$), 2.42 (3H,S, —C—CH$_3$), 3.07–3.97 (4H,m,3-H, S—CH$_2$), 5.23–6.39 (6H,m, HC=CH$_2$, —O—CH$_2$—, 4-H), 5.38 (2H,S, —O—CH$_2$—), 7.57–8.37 (4H,m, —C$_6$H$_4$)

$\nu_{max}$ (CDCl$_3$) 1795, 1732 cm$^{-1}$

EXAMPLE 16b 3.13 g of 3-chloroperbenzoic acid in 20 ml of ethyl acetate were added dropwise over 20 minutes to a stirred solution in 10 ml of ethyl acetate of the 4-nitrobenzyl 3,3-di(acetylthio)-2-(4-allylthioazetidin-2-on-1-yl)propenoate obtained in Example 15b at about −35°. TLC analysis indicated almost complete conversion of the starting material to product. The solution was then evaporated to dryness, slurried with dichloromethane and chromatographed on silica gel using ethyl acetate/hexane mixtures as eluant 1.09 g of pure product was obtained. (35% of the theoretical yield, calculated on the starting material of Example 15b.) For analytical data see Example 16a.

EXAMPLE 17
4-Nitrobenzyl 3-acetylthio-8-oxo-4,5-dithia-1-azabicyclo[4,2,0]oct-2-ene-2-carboxylate

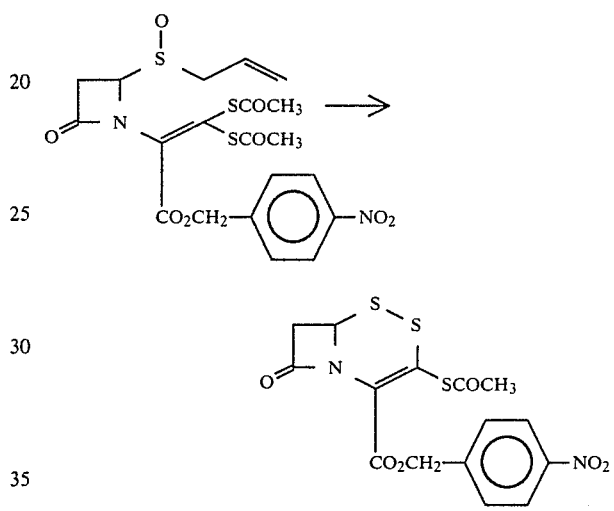

EXAMPLE 17a 0.500 g of 4-nitrobenzyl 3,3-di(acetylthio)-2-(4-allyl-sulphinyl-azetidin-2-on-1-yl)propenoate and 0.192 g of toluenesulphonic acid hydrate were heated under reflux in 25 ml of dioxane with stirring, under argon for 50 minutes, when TLC analysis indicated completion of reaction. The crude product was evaporated to dryness and chromatographed on silica gel using ethyl acetate/hexane mixtures as eluant. 0.192 g (46%) of pure product was obtained.

δ(CDCl$_3$) 2.37 (3H,S,

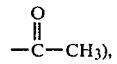

—C—CH$_3$), 3.17 (1H,2d,J$_{trans}$ 3 Hz, 7-H), 3.88 (1H,2d,J$_{cis}$ 5 Hz, J$_{gem}$ 16 Hz, 7-H), 4.88 (1H,2d, 6-H), 5.38 (2H,S, —O—CH$_2$—) 7.50–8.28 (4H,m, —CH$_6$H$_4$)

$\nu_{max}$ (CDCl$_3$) 1793, 1739 cm$^{-1}$ m/e 411.9933 (M+), 43.0209 (COCH$_3$) (base peak)

EXAMPLE 17b

The procedure described in Example 17a was carried out, refluxing 0.300 g of the propenoate and 75.9 μl of boron trifluoride diethyl etherate for 45 minutes. 0.102 g (41%) of purified product was obtained.

EXAMPLE 17c

The procedure described in Example 17a was carried out, using 0.200 g of the propenoate and 98 μl of boron trifluoride diethyl etherate and 50 μl of water in 5 ml of dioxane, and refluxing for 30 minutes. 0.087 g (54%) of purified product was obtained.

EXAMPLE 17d

The procedure described in Example 17a was carried out, refluxing 0.200 g of the propenoate, 45 μl of stannic chloride, 50 μl of water and 5 ml of dioxane for 60 minutes. 0.052 g (32%) of purified product was obtained.

EXAMPLE 18

4-Nitrobenzyl 3-acetylthio-7-oxo-4-thia-1-azabicyclo[3,2,0]hept-2-ene-2-carboxylate

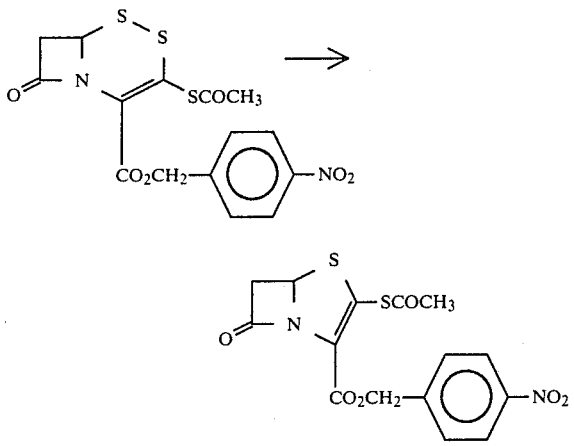

0.186 g of 4-nitrobenzyl 3-acetylthio-8-oxo-4,5-dithia-1-azabicyclo[4,2,0]oct-2-ene-carboxylate was dissolved in 1.5 ml of deuterochloroform and 0.118 g of triphenylphosphine was added. TLC and NMR analysis indicated completion of the reaction. The crude product was chromatographed on silica gel and eluted with ethyl acetate/hexane mixtures. 0.106 g (62%) of pure product was obtained.

m.p. 145° (from ethyl acetate/hexane)
δ(CDCl₃) 2.45 (3H,S,

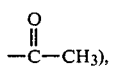
—C—CH₃), 3.55 (1H,2d,J$_{trans}$ 2 Hz, 6-H), 3.93 (1H,2d,J$_{cis}$ 4 Hz, J$_{gem}$ 17 Hz, 6-H) 3.93 (1H,2d,J$_{cis}$ 4 Hz, J$_{gem}$ 17 Hz, 6-H) 5.20 and 5.48 (2H, ABq, J 14 Hz, —O—CH₂—) 5.73 (1H, 2d, 5-H), 7.55–8.32 (4H,m, —C₆H₄)

$v_{max}$ (CDCl₃) 1800, 1714 cm⁻¹
m/e 380.0196 (M+), 43.0210 (COCH₃) (base peak)

EXAMPLE 19

4-Nitrobenzyl 7-oxo-3-thioxo-4-thia-1-azabicyclo[3,2,0]heptane-2-carboxylate

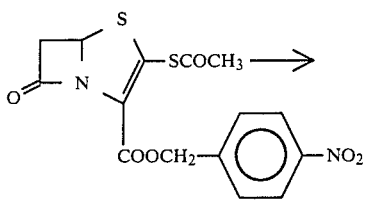

-continued

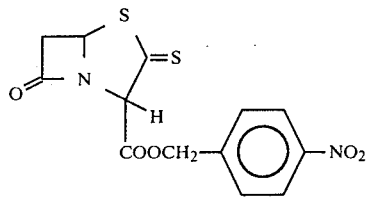

To a stirred solution of 100 mg of 4-nitrobenzyl 3-acetylthio-7-oxo-4-thia-1-azabicyclo[3,2,0]hept-2-ene-2-carboxylate in a mixture of 2 ml of dioxane and 0.2 ml of water was added 19.6 mg of imidazole. After 10 minutes the reaction mixture was diluted with 5 ml of 1M aqueous acid solution and extracted with dichloromethane (2×5 ml). The organic extracts were combined and backwashed with water (2×5 ml), then brine (5 ml), and finally dried and evaporated. The residue was chromatographed on silica gel, with elution by means of ethyl acetate/hexane mixtures. Fractions containing the purified product were combined and evaporated to leave an orange oil (43 mg, 48%).

δ(CDCl₃) 3.5 (1H,2d,J$_{trans}$ 2 Hz, J$_{gem}$ 16 Hz, 6-H), 4.14 (1H,2d,J$_{cis}$ 4 Hz, 6-H), 5.4 (2H,S, —CH₂—), 5.5 (1H,S, —CH), 5.98 (1H,2D, 5-H), 7.5–8.5 (4H,m, —C₆H₄).

ν(CDCl₃) 1800, 1754 cm⁻¹
m/e 338.0003 (M+), 262(M—CS₂), 234(M—CS₂—CO),

136(CH₂—C₆H₄—NO₂), 116 (thiazolium S=S), 76(CS₂),

54(base peak)

76(CS₂), 54(base peak)

EXAMPLE 20

Methyl 7-oxo-3-thioxo-4-thia-1-azabicyclo[3,2,0]heptane-2-carboxylate

To a stirred solution of 120 mg of methyl 3-acetylthio-7-oxo-4-thia-1-azabicyclo[3,2,0]hept-2-ene-2-carboxylate in a mixture of 2 ml of dioxane and 0.2 ml of water were added 32 mg of imidazole. After 15 minutes the reaction mixture was diluted with 5 ml of a 1M aqueous citric acid solution and extracted with ethyl acetate (2×5 ml). The ethyl acetate extracts were evaporated to dryness, the residue slurried with chloroform and washed with water (2×5 ml). The chloroform layers were dried and evaporated to leave a yellow oil (83 mg, 83%).

δ(CDCl$_3$) 3.4 (1H,2d,J$_{trans}$ 2 Hz, J$_{gem}$ 16 Hz, 6-H, 3.8 (3H,S, —CH$_3$), 3.9 (1H,2d,J$_{cis}$ 4 Hz, 6-H) 5.3 (1H,S, 2-H), 5.84 (1H,2d, 5-H).

ν(CDCl$_3$) 1798, 1750 cm$^{-1}$ m/e 216.9875 (M+), 141

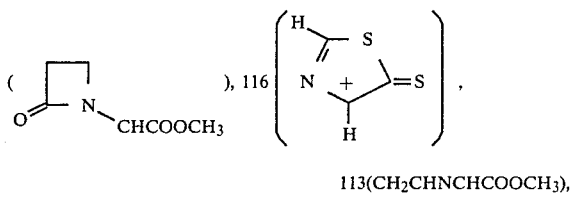

113 (CH$_2$CHNCHCOOCH$_3$), 76 (CS$_2$), 54 (base peak).

EXAMPLE 21

4-Allylthio-3-ethylazetidinone

To a solution of 1.06 g of sodium hydroxide in 14 ml of water were added 2.82 ml of allylthiol. The solution was stirred under an argon atmosphere for 10 minutes. To this solution was added, over a period of 1 minute, a solution of 3.79 g of ethyl acetoxyazetidinone in 6 ml of water. After about 15 minutes, when the starting material had been consumed, the solution was extracted three times with dichloromethane. The combined organic extracts were back-extracted with water, then dried over magnesium sulphate, evaporated in vacuo, and chromatographed over silica gel, eluting with ethyl acetate/hexane mixtures. The main product (2.84 g) was trans 4-allylthio-3-ethylazetidinone, which contained a trace amount of the cis isomer. (Yield 2.84 g)

ν$_{max}$ (CDCl$_3$) 1766 cm$^{-1}$

δ(CDCl$_3$) 1.04 (3H, t, J7 Hz) 1.75 (2H, q, J7 Hz) 2.96-3.18 (1H, m, 3-H) 3.31 (2H, d, J7 Hz) 4.46 (1H, d, J$_{trans}$ 2 Hz, 4-H) 5.04-6.46 (3H, m) 6.81 (1H, s)

EXAMPLE 22

Methyl(4-allylthio-3-ethylazetidin-2-on-1-yl)acetate

To a solution of 2.34 g of 4-allylthio-3-ethylazetidinone in 20 ml of redistilled dimethylformamide were added 1.37 ml of methyl bromoacetate and 4.16 g of ground potassium carbonate. The solution was stirred overnight then filtered through a pad of Hyflo, (Hyflo being a Trade Mark), poured into 75 ml of water, and extracted five times with ethyl acetate. The combined organic extracts were washed with water, dried over magnesium sulphate, and evaporated in vacuo to give the title compound. (Yield 3 g)

ν$_{max}$(CDCl$_3$) 1763, 1748 cm$^{-1}$

δ(CDCl$_3$) 1.07 (3H, t, J7 Hz) 1.77 (2H, q, 7 Hz) 3.04-3.36 (3H, m, 3-H) 3.24 (2H, d, J6 Hz) 3.67 and 4.31 (2H, ABq, J18 Hz) 4.64 (1H, d, J$_{trans}$ 2 Hz, 4-H) 4.94-5.40 (2H, m) 5.55-6.30 (1H, m)

EXAMPLE 23

(4-Allylthio-3-ethylazetidin-2-on-1-yl)acetic acid

To a solution of 3 g of Methyl-(4-allylthio-3-ethylazetidin-2-on-1-yl)acetate in 10 ml of absolute ethanol was added, at room temperature and dropwise over 5 minutes, a solution of 0.90 g of potassium hydroxide in a mixture of 12 ml of ethanol and 1 ml of water. The resulting solution was then poured into 10 ml of dichloromethane, 13 ml of 2M hydrochloric acid and 20 ml of water were added, and the organic phase was separated. The aqueous phase was extracted twice with dichloromethane, and then the combined dichloromethane extracts were re-extracted with aqueous sodium bicarbonate (2.7 mol equivalents in 27 ml) and then discarded. The aqueous bicarbonate layer was then layered with dichloromethane and acidified to pH 1.5 with hydrochloric acid. The aqueous layer was then further extracted with dichloromethane. The combined organic layer was dried over magnesium sulphate and evaporated in vacuo to give the title compound as a colorless crystalline solid. (Yield 2.56 g)

δ(CDCl$_3$) 1.05 (3H, t, J7 Hz) 1.75 (2H, q, 7 Hz) 2.95-3.33 (3H, m, 3-H) 3.19 (2H, d, J6 Hz) 3.65 and 4.29 (2H, ABq, J18 Hz) 4.56 (1H, d, J2 Hz, 4-H) 4.90-5.33 (2H, m) 5.45-6.19 (2H, m) 10.41 (1H, s).

EXAMPLE 24

4-Nitrobenzyl-(4-allylthio-3-ethylazetidin-2-on-1-yl)acetate

To a solution of 2.5 g of (4-allylthio-3-ethylazetidin-2-on-1-yl)acetic acid in 8 ml of dimethylacetamide was added 0.636 g of freshly ground sodium carbonate. After stirring for 20 minutes, 2.591 g of 4-nitrobenzyl bromide were added in one batch. After about 45 minutes, when the starting material had been consumed, the solution was poured into water and extracted three times with ethyl acetate. The combined organic extracts were washed with saturated sodium bicarbonate, water and saturated brine, and then dried over magnesium sulphate, evaporated in vacuo and chromatographed on silica gel, eluting with ethyl acetate/hexane mixtures to give the title compound as a pale yellow oil. (Yield 3.08 g)

ν$_{max}$ (CDCl$_3$) 1750 cm$^{-1}$

δ(CDCl$_3$) 1.05 (3H, t, J7 Hz) 1.78 (2H, q, J7 Hz) 3.06-3.44 (3H, m, 3-H) 3.22 (2H, d, J7 Hz) 3.77 and 4.38 (2H, ABq, J19 Hz) 4.63 (1H, d, J2 Hz, 4-H) 4.93-6.30 (5H,m) 5.20 (2H, s) 7.41-8.50 (4H, m).

EXAMPLE 25

4-Nitrobenzyl-2-(4-allylthio-3-ethylazetidin-2-on-1-yl)-3,3-bis(acetylthio)propenoate To a well stirred solution of 12 g of 4-nitrobenzyl(4-allylthio-3-ethylazetidin-2-on-1-yl)acetate in 75 ml of dry tetrahydrofuran, which was cooled to −78° C. and held under an argon atmosphere, was added a solution of performed lithium hexamethyldisilazane (prepared by adding 45.6 ml of butyllithium to a solution of 15.6 ml of hexamethyl-disilazane in 75 ml of tetrahydrofuran cooled to −20° C. and then cooled to −78° C.). After stirring for 10 minutes, 3.96 ml of carbon disulphide were added in one batch, and stirring was continued for a further 5 minutes. 12.48 ml of acetic anhydride were then added, and the solution was allowed to warm to room temperature. The solution was then extracted using ethyl acetate and water. The aqueous phase was extracted again with ethyl acetate. The combined organic extracts were evaporated in vacuo and chromatographed over silica gel, eluting with ethyl acetate/hexane mixtures to give the title compound as a yellow oil. (Yield 12.19 g)

δ(CDCl$_3$) 1.06 (3H, t, J8 Hz) 1.75 (2H, q, J8 Hz) 2.28 (3H, s) 2.39 (3H, s) 3.12-3.54 (3H, m) 3.35 (2H, d, J7 Hz, 3-H) 5.06 (1H, d, J$_{trans}$ 3 Hz, 4-H) 6.09-6.35 (5H, m) 5.41 (2H, s) 7.54-8.45 (4H, m).

EXAMPLE 26

4-Nitrobenzyl-2-(4-allylsulphinyl-3-ethylazetidin-2-on-1-yl)-3,3-bis(acetylthio)propenoate To a solution, cooled to −45° C., of 0.94 g of 4-nitrobenzyl 2-(4-allylthio-3-ethylazetidin-2-on-1-yl)-3,3-bis-(acetylthio)propenoate in 10 ml of ethyl acetate was added portionwise a solution of 0.386 g of m-chloroperbenzoic acid in 10 ml of ethyl acetate. When the reaction was complete, the solution was diluted with ethyl acetate, and then washed with potassium metabisulphite, with saturated sodium bicarbonate, with water, and finally with saturated brine. The resulting solution was dried over magnesium sulphate and evaporated in vacuo to give the title compound. (Yield 0.96 g).

δ(CDCl$_3$) 0.84–1.30 (3H, m) 2.25 (3H, s) 2.39 (3H, s) 3.23–3.70 (3H, m) 3.24–3.71 (2H, m) 3.47 (2H, d, J6 Hz) 4.97 (1H, d, J$_{trans}$ 3 Hz, 4-H) 5.15–6.21 (5H, m) 5.35 (2H, s) 7.39–8.40 (4H, m)

EXAMPLE 27

4-Nitrobenzyl 7-ethyl-8-oxo-3-acetylthio-4,5-dithia-1-azabicyclo[4,2-0]oct-2-ene-2-carboxylate To a solution of 0.96 g of 4-nitrobenzyl 2-(4-allyl-sulphinyl-3-ethylazetidin-2-on-1-yl)-3,3-bis(acetylthio)-propenoate in 25 ml of dioxane were added 0.52 ml of ethanol and 0.44 ml of boron trifluoride diethyletherate.

The solution, which was held under a positive pressure of argon, was placed in an oil bath preheated to 130° C., and allowed to reflux. When the sulphoxide had been consumed, the solution was cooled quickly, and was then diluted with ethyl acetate, washed with water and then with saturated brine, and was then dried, and evaporated in vacuo to yield the title compound in crude form as an orange-yellow gum. (Yield 0.90 g).

δ (CDCl$_3$) 0.86–1.34 (3H, m) 1.75–2.22 (2H, m) 2.36 (3H, s) 3.13–3.76 (1H, m. 7-H) 4.65 (1H, d, J$_{trans}$ 3 Hz, 6-H) 5.40 (2H, s) 7.49–8.44 (4H, m)

EXAMPLE 28

4-Nitrobenzyl 6-ethyl-7-oxo-3-acetylthio-4-thia-1-azabicyclo[3,2,0-]hept-2-ene-2-carboxylate To a solution of 0.90 g of 4-nitrobenzyl 7-ethyl-8-oxo-3-acetylthio-4,5-dithia-1-azabicyclo[4,2,0]oct-2-ene 2-carboxylate in 2 ml of dichloromethane was added, in one batch, a solution of 0.59 g of triphenylphosphine in 3 ml of dichloromethane. After 10 minutes, the reaction mixture was chromatographed directly on silica gel, eluting with ethyl acetate/hexane mixtures, to give the title compound as a yellow crystalline solid. (Yield 0.25 g)

δ (CDCl$_3$) 1.02 (3H, t, J7 Hz) 1.93 (2H, q, J7 Hz) 2.40 (3H, s) 3.45–4.14 (1H, m, 6-H) 5.07 and 5.39 (2H, ABq, J14 Hz) 5.65 (1H, d, J$_{cis}$ 4 Hz, 5-H) 7.27–8.16 (4H, m).

EXAMPLE 29

4-Nitrobenzyl 6-ethyl-7-oxo-3-thioxo-4-thia-1-azabicyclo[3,2,0]heptane 2-carboxylate To a stirred solution of 0.25 g of 4-nitrobenzyl 6-ethyl-7-oxo-3-acetylthio-4-thia-1-azabicyclo[3,2,0]hept-2-ene 2-carboxylate in 4 ml of dioxan and 0.5 ml of water was added, in one batch, 0.046 g of imidazole. After 10 minutes, the solution was diluted with 10 ml of 1M citric acid and extracted twice with dichloromethane. The combined organic extracts were washed with water, dried over magnesium sulphate, and evaporated in vacuo to give the title compound in a quantitative yield.

δ (CDCl$_3$) 1.04 (3H, t, J7 Hz) 1.81 (2H, q, J7 Hz) 3.53–4.08 (1H, m, 6-H) 5.22–5.39 (3H, m, 2-H) 5.28 (2H, s) 5.99 (1H, d, J$_{cis}$ 5 Hz, 5-H) 7.35–8.33 (4H, m).

EXAMPLE 30

4(R)-Allylthio-3(S)-[1(R)-{dimethyl-{2-methylprop-2-yl}silyloxy}ethyl]azetidin-2-one To a stirred solution of 1.14 ml of allyl mercaptan and 0.4 g of sodium hydroxide in 25 ml of water under an argon atmosphere was added a solution of 2.87 g of 4-acetoxy-3(S)-[1(R)-{dimethyl-{2-methylprop-2-yl}silyloxy}ethyl]azetidin-2-one in 10 ml of methanol. After 30 minutes, the mixture was partitioned between dichloromethane and water. The separated organic layer was washed with water, was dried over magnesium sulphate, evaporated to dryness, and then chromatographed on silica gel. Elution with ethyl acetate/hexane mixtures afforded 1.8 g of the title compound as white crystals.

ν$_{(max)}$CDCl$_3$ 3420, 1767 cm$^{-1}$

δ (CDCl$_3$) 0.05 (6H, s) 0.88 (9H, s) 1.20 (3H, d, J6 Hz) 2.9–3.2 (3H, m) 3.9–4.3 (1H, m, H-1') 4.84 (1H, d J$_{3,4}$ 2 Hz, H-4) 4.95–6.3 (3H, m) 7.28 (1H, broad s)

EXAMPLE 31a

Methyl 2-(4-(R)-allylthio-3(S)-[1(R)-{dimethyl-{2-methylprop-2-yl}silyloxy}ethyl]azetidin-2-on-1-yl)acetate To a stirred solution of 1.76 g of 4(R)-allylthio-3(S)9-[1(R)-{dimethyl-{2-methylprop-2-yl}silyloxy}ethyl-]azetidin-2-one in 60 ml of dry dimethylformamide were added 3.52 g of finely ground potassium carbonate and 0.6 ml of methyl bromoacetate. After 18 hours, the mixture was filtered and then partitioned between ethyl acetate and water. The separated organic layer was washed with water and dried over magnesium sulphate. Evaporation in vacuo afforded a crude product which was chromatographed on silica gel. Elution with ethyl acetate/hexane mixtures afforded 1.56 g of the title compound as a pale yellow oil.

ν$_{max}$CDCl$_3$ 1753, 1768 cm$^{-1}$

δ (CDCl$_3$) 0.06 (6H, s) 0.86 (9H, s) 1.23 (3H, d J6.5 Hz) 3.2 (3H, m) 3.70 (3H, s) 3–6–4.3 (3H, m) 4.87 (1H, d J 2 Hz, H-4) 4.9–6.3 (3H, m).

EXAMPLE 31b

Methyl 2-(4(S)-allylthio-3(S)-[1(R)-{dimethyl{2-methylprop-2-yl}silyloxy}ethyl]azetidin-2-on-1-yl)acetate This compound was prepared analogously to its 4(R) isomer, as described in Example 31a, using the corresponding 4(S) starting material.

EXAMPLE 32a

4-Nitrobenzyl 2-(4(R)-allylthio-3(S)-[1(R)-{dimethyl{2-methylprop-2-yl}silyloxy}ethyl]azetidin-2-on-1-yl)acetate To a stirred solution of 3.04 g of potassium hydroxide in 80 ml of 95% ethanol was added a solution of 16 g of methyl 2-(4(R)-allylthio-3(S)-[1(R)-{dimethyl-{2-methylprop-2-yl}silyloxy}ethyl]azetidin-2-on-1-yl)acetate. After 10 minutes, the mixture was evaporated to about 1/5 of its original volume; 2 ml of dimethyl acetamide were added, followed by a solution of 9.25 g of 4-nitrobenzyl bromide in 50 ml of dimethylacetamide. After 1 hour, the mixture was partitioned between 0.01M HCl and ethyl acetate. The separated organic layers were washed with 0.01M HCl, with water, with cold, saturated sodium bicarbonate, and with brine, and were then dried and evaporated. The resulting crude product was chromatographed over silica gel; elution with ethyl acetate/hexane mixtures afforded 19.5 g of the title compound as an oil.

$\nu_{max}$(CDCl$_3$) 1755, 1769 cm$^{-1}$

δ (CDCl$_3$) 0.07 and 0.09 (6H, two singlets) 0.88 (9H, s) 1.25 (3H, d J6 Hz) 3.2 (3H, m) 3.7–4.5 (3H, m) 4.95 (1H, d J2 Hz, H-4) 4.9–6.3 (5H, m) 7.5–8.35 (4H, m)

EXAMPLE 32b

4-Nitrobenzyl-2-(4(S)-allylthio-3(S)-[1(R)-{dimethyl{2-methylprop-2-yl}silyloxy}ethyl]azetidin-2-on-1-yl)acetate This compound was prepared analogously to its 4(R) isomer, as described in Example 32a, using the corresponding 4(S) starting material.

EXAMPLE 33a

4-Nitrobenzyl 3,3-bis(acetylthio)-2-(3(S)-allylthio-[1(R)-{dimethyl-{2-methylprop-2-yl}silyloxy}ethyl]azetidin-2-on-1-yl)propenoate A solution of lithium hexamethyldisilazide was prepared by the addition of n-butyllithium in hexane (2.79 ml of a 1.6M solution) to 0.982 ml of hexamethyldisilazane in 8 ml of dry tetrahydrofuran at −10° C., while stirring under argon. The solution was cooled to −78° C. and added by cannula to a solution of 0.98 g of 4-nitrobenzyl 2-(4(R)-allylthio-3(S)-[1(R)-{dimethyl-{2-methylprop-2-yl}silyloxy}ethyl]azetidin-2-on-1-yl)acetate in 8 ml of dry tetrahydrofuran at 78° C., with stirring under argon. After 5 minutes, 0.357 ml of carbon disulphide was added by syringe, followed by 0.748 ml of acetic anhydride. The mixture was allowed to warm to room temperature, and 30 ml of dichloromethane were added, followed by 30 ml of water. The organic layer was separated, and the aqueous layer was extracted with further dichloromethane. The combined organic extracts were washed with 1M HCl, with water, and with a 12% sodium chloride solution, and were then dried over magnesium sulphate and evaporated to give 1.38 g of an orange oil. 1.21 g of this crude product was chromatographed on silica gel using ethyl acetate/hexane mixtures as eluant to give 0.800 g of the title compound in purified form.

δ(CDCl$_3$) 0.10 (6H, s) 0.88 (9H, s) 1.35 (3H, d, J7 Hz) 2.24 (3H, s) 2.37 (3H, s) 3.15–3.64 (3H, m, 3-H) 3.30 (2H, d, J7 Hz) 4.00–4.46 (1H, m) 4.91–6.21 (6H, m) 5.30 (2H, s) 7.40–8.36 (4H, m).

EXAMPLE 33b

4-Nitrobenzyl 3,3-di(acetylthio)-2-((3S,4R)-4-allylthio-3-[1(R)-{dimethyl-{2-methylprop-2-yl}silyloxy}ethyl]azetidin-2-on-1-yl)propenoate The above compound was prepared analogously to its 4(S) isomer, as described in Example 33a, using the corresponding 4(R) starting material.

$\nu_{max}$(CDCl$_3$) 1778, 1745 cm$^{-1}$

δ (CDCl$_3$) 0.06 (6H, s) 0.85 (9H, s) 1.26 (3H, d, J6 Hz) 2.25 (3H, s) 2.35 (3H, s) 3.11–3.52 (3H, m, 3-H) 3.35 (2H, d, J6 Hz) 4.14-4.39 (1H, m) 4.95–6.30 (6H, m) 5.35 (2H, s) 5.56 (1H, d, J3 Hz, 4-H) 7.44–8.38 (4H, m).

EXAMPLE 34a

4-Nitrobenzyl 3,3-di(acetylthio)-2-((3S,4S)4-allylsulphinyl-3-[1(R)-{dimethyl-{2-methylprop-2-yl}silyloxy}ethyl]azetidin-2-on-1-yl)propenoate 0.080 g of 3-chloroperbenzoic acid in 2 ml of ethyl acetate was added dropwise over 3 minutes to a stirred solution of 0.200 g of 4-nitrobenzyl 3,3-di(acetylthio)-2-((3S,4S)4-allylthio-3-[1(R)-{dimethyl-{2-methylprop-2-yl}silyloxy}ethyl]azetidin-2-on-1-yl propenoate in 3 ml of ethyl acetate at 35° C. The organic solution was washed with a potassium metabisulphite solution (0.5 g in 5 ml), with saturated sodium bicarbonate solution and then with 12% brine. The resulting organic solution was then dried over magnesium sulphate and evaporated to give a pale yellow foam. 0.205 g of the title compound was obtained.

δ(CDCl$_3$) 0.12 (6H, s) 0.90 (9H, s) 1.20–1.60 (3H, m) 2.26 (3H, s) 2.40 (3H, s) 3.39–4.01 (3H, m, 3-H) 3.57 (2H, d, J6 Hz) 4.37–4.85 (1H, m) 5.15 and 5.19 (1H, 2d, J$_{4\beta,3\beta}$6 Hz, 4-H) 5.22–6.28 (5H, m) 5.36 (2H, s) 7.45–8.45 (4H, m).

EXAMPLE 34b

4-Nitrobenzyl 3,3-di(acetylthio)-2-((3S,4R)4-allylsulphinyl-3-[1(R)-{dimethyl-{2-methylprop-2-}silyloxy}ethyl]azetidin-2-on-1-yl)propenoate The above compound was prepared analogously to its 4(S) isomer, as described in Example 34a, using the corresponding 4(R) starting material.

EXAMPLE 35a

4-Nitrobenzyl 6(S), 3-acetylthio-7(S)-[1(R)-hydroxyethyl]-8-oxo-4,5-dithia-1-azabicyclo[4,2,0]oct-2-en-2-carboxylate To a solution of 0.205 g of 4-nitrobenzyl 3,3-di(acetylthio)-2-((3S,4S)-4-allylsulphinyl-3-[1(R)-{dimethyl{2-methylprop-2-yl}silyloxy}ethyl]-2-azetidin-2-on-1-yl)propenoate in 5 ml of dioxane were added 27 μl of water followed by 61 μl of boron trifluoride diethyletherate. The mixture was then heated rapidly to reflux with stirring and under an argon atmosphere for 40 minutes. 5 ml of water were added to the reaction mixture, which was then extracted with ethyl acetate. The organic phase was washed with water, dried over magnesium sulphate, evaporated, and chromatographed on silica gel using ethyl acetate/hexane mixtures as eluant. 0.047 g of the title compound was obtained.

$\nu_{max}$(CDCl$_3$) 1783, 1739 cm$^{-1}$

δ (CDCl$_3$) 1.45 (3H, d, J6 Hz) 2.23 (1H, s) 2.38 (3H, s) 3.97 (1H, 2d, J6 Hz, J10 Hz, 7-H) 4.22–4.65 (1H, m) 5.20–1H, d, 6-H) 5.41 (2H, s) 7.46–8.46 (4H, m)

EXAMPLE 35b

4-Nitrobenzyl 6(R), 3-acetylthio-7(S)-[1(R)-hydroxyethyl]-8-oxo-4,5-dithia-1-azabicyclo[4,2,0]oct-2-en-2-carboxylate This compound was prepared analogously to its 6(S) isomer, as described in Example 35a, using the corresponding 4(R) starting material (described in Example 34b).

EXAMPLE 36a

4-Nitrobenzyl 3-acetylthio-6(S)-[1(R)-hydroxy ethyl]-7-oxo-4-thia-1-azabicyclo[3,2,0]hept-2-ene-2-carboxylate 0.121 g of 4-nitrobenzyl 6(S), 3-acetylthio-7(S)-[1(R)-hydroxyethyl]-8-oxo-4,5-dithia-1-azabicyclo[4,2,0]oct-2-en-2-carboxylate was dissolved in 3 ml of deuterochloroform and 0.070 g of triphenylphosphine was added, with stirring at room temperature. After 5 minutes, the crude product was chromatographed on silica gel using dichloromethane/hexane and ethyl acetate/dichloromethane mixtures as eluant. 0.039 g of a mixture of the 5R and 5S isomers of the title compound was obtained.

δ (CDCl$_3$) 1.37 and 1.48 (3H, 2d, J7 Hz) 2.00 (1H, s) 2.46 (3H, s) 3.52–4.12 (1H, m, 6-H)4.12–4.57 (1H, m) 5.07–5.69 (2H, m) 5.75 and 5.81 (1H, 2d, J$_{5\alpha,6\beta}$2 Hz J$_{5\beta,6\beta}$5 Hz, 5-H) 7.54–8.46 (4H, m, —C$_6$H$_4$)

EXAMPLE 36b

4-Nitrobenzyl 3-acetylthio-6(S)-[1(R)-hydroxyethyl]-7-oxo-4-thia-1-azabicyclo[3,2,0]hept-2-ene-2-carboxylate This compound was prepared analogously as described in Example 36a using the corresponding 6(R) starting material (described in Example 35b). A mixture of the 5(R) and 5(S) isomers was obtained.

EXAMPLE 37

4-Nitrobenzyl 6(S)-[1(R)-hydroxyethyl]-7-oxo-3-thioxo-4-thia-1-azabicyclo[3,2,0]heptane-2-carboxylate To a stirred solution of 0.039 g of 4-nitrobenzyl 3-acetylthio-6(S)-(1(R)-hydroxyethyl)-7-oxo-4-thia-1-azabicyclo[3,2,0]hept-2-en-2-carboxylate in a mixture of 1.5 ml of dioxan and 0.15 ml of water was added 0.0069 g of imidazole at room temperature. After 5 minutes the mixture was diluted with 3 ml of 1M hydrochloric acid and 5 ml of water, and then extracted into ethyl acetate. The combined organic extracts were washed with water and dried over magnesium sulphate. The resulting solution was evaporated to give a mixture of the 5R and 5S isomers of the title compound as a foam.

ν$_{max}$(CDCl$_3$) 1790, 1753 cm$^{-1}$

δ (CDCl$_3$) 1.10–1.61 (3H, m) 2.28 (1H, s) 3.57–4.05 (1H, m, 6-H) 4.14–4.52 (1H, m) 5.35 (2H, s) 5.41 (1H, s, 2-H) 5.89 and 6.06 (1H, 2d, J$_{5\alpha,6\beta}$1 Hz, J$_{5\beta,6\beta}$4 Hz, 5-H) 7.35–8.40 (4H, m, —C$_6$H$_4$)

EXAMPLE 38

4-Nitriobenzyl 6-ethyl-3-ethylthio-7-oxo-4-thia-1-azabicyclo[3,2,0]hept-2-ene 2-carboxylate To a solution of 0.5 g of 4-nitrobenzyl 6-ethyl-7-oxo-3-thioxo-4-thia-1-azabicyclo[3,2,0]heptane 2-carboxylate in 2 ml of dioxane was added, in one batch, 0.57 ml of N-ethyldiisopropylamine, then 0.10 ml of bromoethane. When the reaction was complete, the solution was evaporated in vacuo and chromatographed on silica gel, eluting with ethyl acetate/hexane mixtures to give the title product. (Yield 0.300 g)

ν$_{max}$(CDCl$_3$) 1789 cm$^{-1}$

δ (CDCl$_3$) 0.85–1.49 (6H, m) 1.77–2.26 (4H, m) 3.58–4.12 (1H, m, 6-H) 5.16 and 5.50 (2H, AB$_q$, J14 Hz) 5.41 and 5.77 (1H, 2d, J$_{trans}$2 Hz, J$_{cis}$ 5 Hz, 5-H) 7.41–8.31 (4H, m).

EXAMPLE 39

4-Nitrobenzyl 3-ethylthio-6(S)-[1(R)hydroxyethyl]-7-oxo-4-thia-1-azabicyclo[3,2,0]hept-2-en-2-carboxylate To 0.200 ml of diisopropylamine was added to 0.426 g of 4-nitrobenzyl 6(S)-[1(R)-hydroxyethyl]-7-oxo-3-thio-4-thia-1-azabicyclo[3,2,0]heptane-2-carboxylate in dry tetrahydrofuran with stirring. 0.252 ml of iodoethane was then added and stirring was continued for 16 hours at room temperature. The reaction mixture was then evaporated to dryness and chromatographed on silica gel, eluting with ethyl acetate/hexane mixtures, to give the title product as a mixture of 5R and 5S isomers.

δ (CDCl$_3$) 1.38 (3H, d J6 Hz) 1.39 (3H, t) 2.02 (1H, s) 2.97 (2H, q) 3.64–3.81 (1H, m, 6-H) 3.85–4.52 (1H, m) 5.15 and 5.48 (2H, AB$_q$) 5.64 (1H, d J1 Hz, 5-H) 7.48–8.33 (4H, ABq).

EXAMPLE 40

4-Nitrobenzyl 3-ethylthio-7-oxo-4-thia-1-azabicyclo[3,2,0]hept-2-ene 2-carboxylate To a solution of 0.5 g of 4-Nitrobenzyl 7-oxo-3-thio-4-thia-1-azabicyclo[3,2,0]heptane 2-carboxylate in 2 ml of dioxane and 0.25 ml of water was added, in one batch, 0.57 ml of N-ethyldiisopropylamine and then 0.11 ml of bromoethane. When the reaction was complete the solution was evaporated in vacuo and chromatographed on silica gel, eluting with ethyl acetate/hexane mixtures, to give 0.19 g of the title compound ν$_{max}$(CDCl$_3$) 1791 cm$^{-1}$ δ (CDCl$_3$) 1.25 (3H, t, J7 Hz) 3.45 (1H, 2d, J$_{trans}$2 Hz) 3.86 (1H, 2d, J$_{cis}$4 Hz, J$_{gem}$16 Hz) 4.08 (2H, q, J7 Hz) 5.13 and 5.43 (2H, d, J14 Hz) 5.66 (1H, 2d) 7.37–8.22 (4H, m).

We claim:

1. A compound of the formula

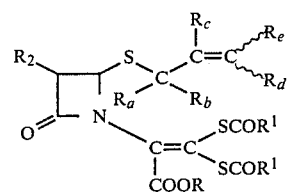

wherein

R is a carboxyl esterifying group removable by hydrolysis, photolysis, reduction, or enzyme action without substantial degradation of the rest of the molecule to give the free acid;

R$^1$ is lower alkyl or phenyl;

R$^2$ is hydrogen, lower alkyl, lower alkoxyalkyl, lower alkanoyloxyalkyl, or tri-lower alkylsilyloxyalkyl;

R$_a$, R$_b$, R$_c$, R$_d$, and R$_e$, taken alone, are the same or different and are hydrogen, alkyl or alkenyl having up to 8 carbon atoms, cycloalkyl or cycloalkenyl having up to 18 carbon atoms, halogen, cyano, carboxyl, or carboxyl esterified with an unsubstituted aliphatic alcohol having up to 20 carbon atoms;

any two of R$_a$, R$_b$, R$_c$, R$_d$, and R$_e$, taken together with the carbon atom or atoms to which they are attached, may form a cycloaliphatic ring having 3 to 10 carbon atoms, said compound having none, one, or two of such rings present therein;
$R_c$ is cis or trans with respect to $R_d$; and
$R^2$ is cis or trans with respect to
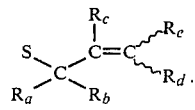
* * * * *